(12) United States Patent
Dahl et al.

(10) Patent No.: US 9,877,672 B2
(45) Date of Patent: Jan. 30, 2018

(54) SAMPLING AND TESTING DEVICE FOR THE HUMAN OR ANIMAL BODY

(75) Inventors: Steven David Dahl, East Brisbane (AU); Sean Andrew Parsons, East Brisbane (AU); Jennifer Maschmann, Blackburn North (AU); Kon Euan Gerard Wong, Burwood East (AU); Tim Ian Spink, Box Hill (AU); Stephen Robert Wilson, Kew (AU)

(73) Assignee: Ellume Pty Ltd, East Brisbane (AU)

( * ) Notice: Subject to any disclaimer, the term of this patent is extended or adjusted under 35 U.S.C. 154(b) by 1300 days.

(21) Appl. No.: 13/575,999

(22) PCT Filed: Jan. 27, 2011

(86) PCT No.: PCT/AU2011/000085
§ 371 (c)(1),
(2), (4) Date: Dec. 21, 2012

(87) PCT Pub. No.: WO2011/091473
PCT Pub. Date: Aug. 4, 2011

(65) Prior Publication Data
US 2013/0096400 A1    Apr. 18, 2013
US 2014/0296667 A9    Oct. 2, 2014

(30) Foreign Application Priority Data

Jan. 28, 2010 (AU) .............................. 2010900329
Feb. 11, 2010 (AU) .............................. 2010900557
May 18, 2010 (AU) .............................. 2010902158

(51) Int. Cl.
*A61B 5/1455* (2006.01)
*A61B 5/15* (2006.01)
(Continued)

(52) U.S. Cl.
CPC .............. *A61B 5/15* (2013.01); *A61B 5/0071* (2013.01); *A61B 5/207* (2013.01);
(Continued)

(58) Field of Classification Search
None
See application file for complete search history.

(56) References Cited

U.S. PATENT DOCUMENTS

| | | | |
|---|---|---|---|
| 4,338,305 | A | 7/1982 | Corbin |
| 4,999,287 | A | 3/1991 | Allen et al. |

(Continued)

FOREIGN PATENT DOCUMENTS

| | | | |
|---|---|---|---|
| CA | 2 496 986 A1 | 10/2005 | |
| CA | 2 802 318 A1 | 1/2012 | |

(Continued)

OTHER PUBLICATIONS

U.S. Appl. No. 13/861,513, filed Apr. 12, 2013, Dahl et al.
(Continued)

*Primary Examiner* — Eric Winakur
*Assistant Examiner* — Marjan Fardanesh
(74) *Attorney, Agent, or Firm* — Wolf, Greenfield & Sacks, P.C.

(57) ABSTRACT

A device (1) is provided that is configured to indicate the presence or absence of one or more biological entities in a biological sample. The device comprises a sampling portion (11), the sampling portion comprising flexible material adjustably conformable to a part of a human or animal body, at least a portion of the sampling portion being absorbent and configured to receive a biological sample directly from the body; and a test portion (12) in fluid engagement with the sampling portion, the test portion comprising one or more test zones (14). The sampling portion and test portion are configured such that at least a portion of the sample received (Continued)

by the sampling portion is transferable to the test portion such as to contact one or more of the test zones, and wherein each test zone is configured to indicate the presence or absence of one or more biological entities in the sample.

23 Claims, 10 Drawing Sheets

(51) Int. Cl.
  *A61B 10/00* (2006.01)
  *A61B 5/00* (2006.01)
  *A61B 5/20* (2006.01)

(52) U.S. Cl.
  CPC ...... *A61B 10/0038* (2013.01); *A61B 10/0045* (2013.01); *A61B 10/0048* (2013.01); *A61B 10/0051* (2013.01); *A61B 10/0058* (2013.01); *A61B 10/0064* (2013.01); *A61B 2010/0003* (2013.01)

(56) References Cited

U.S. PATENT DOCUMENTS

| | | |
|---|---|---|
| 5,418,136 A | 5/1995 | Miller et al. |
| 5,503,985 A | 4/1996 | Cathey et al. |
| 5,525,520 A | 6/1996 | Dinh |
| 5,629,214 A | 5/1997 | Crosby |
| 5,783,399 A | 7/1998 | Childs et al. |
| 5,786,220 A | 7/1998 | Pronovost et al. |
| 5,824,268 A | 10/1998 | Bernstein et al. |
| 5,902,982 A | 5/1999 | Lappe |
| 5,939,252 A | 8/1999 | Lennon et al. |
| 5,942,407 A | 8/1999 | Liotta et al. |
| 5,998,220 A | 12/1999 | Chandler |
| 6,033,627 A | 3/2000 | Shields et al. |
| 6,136,610 A | 10/2000 | Polito et al. |
| 6,248,294 B1 | 6/2001 | Nason |
| 6,267,722 B1 | 7/2001 | Anderson et al. |
| 6,319,665 B1 | 11/2001 | Zwanziger et al. |
| 6,319,965 B1 | 11/2001 | Kamohara et al. |
| 6,365,417 B1 | 4/2002 | Fleming et al. |
| 6,454,705 B1 | 9/2002 | Cosentino et al. |
| 6,549,275 B1 | 4/2003 | Pozniak et al. |
| 6,627,459 B1 | 9/2003 | Tung et al. |
| 6,656,745 B1 | 12/2003 | Cole |
| 6,764,849 B2 | 7/2004 | Small et al. |
| 6,886,864 B2 | 5/2005 | Nelson et al. |
| 6,991,940 B2 | 1/2006 | Carroll et al. |
| 6,998,273 B1 | 2/2006 | Fleming et al. |
| 7,044,919 B1 | 5/2006 | Catt et al. |
| 7,070,920 B2 | 7/2006 | Spivey et al. |
| 7,214,542 B2 | 5/2007 | Hutchinson |
| 7,220,597 B2 | 5/2007 | Zin et al. |
| 7,279,136 B2 | 10/2007 | Takeuchi et al. |
| 7,280,201 B2 | 10/2007 | Helbing |
| 7,300,800 B2 | 11/2007 | Bell et al. |
| 7,315,378 B2 | 1/2008 | Phelan et al. |
| 7,459,314 B2 | 12/2008 | Guo et al. |
| 7,460,222 B2 | 12/2008 | Kalveram et al. |
| 7,486,396 B2 | 2/2009 | Oldham et al. |
| 7,488,450 B2 | 2/2009 | Matusewicz et al. |
| 7,489,403 B1 | 2/2009 | Lin et al. |
| 7,553,453 B2 | 6/2009 | Gu et al. |
| 7,616,315 B2 | 11/2009 | Sharrock et al. |
| 7,651,851 B2 | 1/2010 | Clarke et al. |
| 7,682,801 B2 | 3/2010 | Esfandiari |
| 7,688,440 B2 | 3/2010 | Clarke et al. |
| 7,740,801 B2 | 6/2010 | Saini et al. |
| 7,763,454 B2 | 7/2010 | Nazareth et al. |
| 7,803,322 B2 | 9/2010 | Borich et al. |
| 7,815,854 B2 | 10/2010 | Cohen |
| 7,879,597 B2 | 2/2011 | Esfandiari |
| 7,879,624 B2 | 2/2011 | Sharrock |
| 7,927,561 B2 | 4/2011 | Kirakossian et al. |
| 7,941,376 B2 | 5/2011 | Peckover |
| 8,003,060 B2 | 8/2011 | Cracauer et al. |
| 8,018,593 B2 | 9/2011 | Tan et al. |
| 8,030,091 B2 | 10/2011 | Jerome et al. |
| 8,040,494 B2 | 10/2011 | Ermantraut et al. |
| 8,093,057 B2 | 1/2012 | Choi et al. |
| 8,101,431 B2 | 1/2012 | McDevitt et al. |
| 8,105,552 B2 | 1/2012 | Xiao et al. |
| 8,105,794 B2 | 1/2012 | Shaari |
| 8,105,849 B2 | 1/2012 | McDevitt et al. |
| 8,110,392 B2 | 2/2012 | Battrell et al. |
| 8,128,871 B2 | 3/2012 | Petruno et al. |
| 8,133,671 B2 | 3/2012 | Williams et al. |
| 2001/0021536 A1 | 9/2001 | Lee |
| 2002/0004246 A1 | 1/2002 | Daniels et al. |
| 2002/0031839 A1 | 3/2002 | McNierney et al. |
| 2002/0111741 A1 | 8/2002 | Abraham-Fuchs et al. |
| 2002/0150501 A1 | 10/2002 | Robertson et al. |
| 2003/0032199 A1 | 2/2003 | Meusel et al. |
| 2003/0049175 A1 | 3/2003 | Buechler et al. |
| 2003/0119030 A1 | 6/2003 | Zilber |
| 2004/0019301 A1 | 1/2004 | Wong et al. |
| 2004/0119591 A1 | 6/2004 | Peeters |
| 2004/0151632 A1 | 8/2004 | Badley et al. |
| 2005/0095697 A1 | 5/2005 | Bachur et al. |
| 2005/0130120 A1 | 6/2005 | Lambotte et al. |
| 2005/0136553 A1 | 6/2005 | Kaylor |
| 2005/0196318 A1 | 9/2005 | Matusewicz et al. |
| 2005/0208593 A1 | 9/2005 | Vail et al. |
| 2005/0221505 A1 | 10/2005 | Petruno et al. |
| 2006/0019265 A1 | 1/2006 | Song et al. |
| 2006/0025732 A1* | 2/2006 | Ying .................. A61F 13/84 604/361 |
| 2006/0216832 A1 | 9/2006 | Nishikawa et al. |
| 2006/0246513 A1* | 11/2006 | Bohannon ............ G01N 33/558 435/7.1 |
| 2006/0257992 A1 | 11/2006 | McDevitt et al. |
| 2006/0263244 A1 | 11/2006 | Rannikko et al. |
| 2007/0015285 A1 | 1/2007 | Catt et al. |
| 2007/0031283 A1 | 2/2007 | Davis et al. |
| 2007/0081920 A1 | 4/2007 | Murphy et al. |
| 2007/0184495 A1 | 8/2007 | Shaari |
| 2007/0231923 A1 | 10/2007 | Cumberland et al. |
| 2007/0298436 A1 | 12/2007 | Lappe |
| 2008/0102473 A1 | 5/2008 | Fouquet et al. |
| 2008/0113391 A1 | 5/2008 | Gibbons et al. |
| 2008/0113427 A1* | 5/2008 | Kikta ................. A61B 10/0038 435/287.6 |
| 2008/0311003 A1 | 12/2008 | Chiu |
| 2009/0035743 A1 | 2/2009 | Minter et al. |
| 2009/0061507 A1 | 3/2009 | Ho |
| 2009/0155811 A1 | 6/2009 | Natan et al. |
| 2009/0197296 A1 | 6/2009 | Martin et al. |
| 2009/0192820 A1 | 7/2009 | Bodlaender et al. |
| 2009/0202388 A1 | 8/2009 | Matusewicz et al. |
| 2009/0027501 A1 | 11/2009 | Bonner |
| 2009/0298059 A1 | 12/2009 | Gumbrecht et al. |
| 2009/0314946 A1 | 12/2009 | Song et al. |
| 2010/0009430 A1 | 1/2010 | Wan et al. |
| 2010/0055721 A1 | 3/2010 | Lambert et al. |
| 2010/0087749 A1 | 4/2010 | Tovey et al. |
| 2010/0121156 A1 | 5/2010 | Yoo |
| 2010/0135857 A1 | 6/2010 | Hunter et al. |
| 2010/0176279 A1 | 7/2010 | Lai |
| 2010/0239460 A1 | 9/2010 | Nazareth et al. |
| 2010/0240149 A1 | 9/2010 | Nazareth et al. |
| 2010/0248277 A1 | 9/2010 | Gibbons et al. |
| 2010/0272635 A1 | 10/2010 | Rodems et al. |
| 2010/0291588 A1 | 11/2010 | McDevitt et al. |
| 2010/0304397 A1 | 12/2010 | Burns et al. |
| 2011/0038767 A1 | 2/2011 | Baril |
| 2011/0151584 A1 | 6/2011 | Esfandiari |
| 2011/0178723 A1 | 7/2011 | Charrock et al. |
| 2011/0195441 A1 | 8/2011 | Hemker et al. |
| 2011/0213564 A1 | 9/2011 | Henke |
| 2011/0213579 A1 | 9/2011 | Henke |
| 2011/0213619 A1 | 9/2011 | Henke |
| 2011/0266462 A1 | 11/2011 | Doi |
| 2011/0294199 A1 | 12/2011 | Bearinger et al. |

(56) References Cited

U.S. PATENT DOCUMENTS

| | | |
|---|---|---|
| 2012/0015448 A1 | 1/2012 | Sharrock |
| 2012/0096400 A1 | 4/2012 | Cho |
| 2012/0129272 A1 | 5/2012 | Petruno et al. |
| 2013/0280795 A1 | 10/2013 | Dahl et al. |
| 2014/0296667 A9 | 10/2014 | Dahl et al. |
| 2015/0204891 A1 | 7/2015 | Parsons |
| 2015/0241455 A1 | 8/2015 | Parsons |

FOREIGN PATENT DOCUMENTS

| | | |
|---|---|---|
| CN | 101137897 A | 3/2008 |
| CN | 101551398 A | 10/2009 |
| DE | 103 35 611 A1 | 3/2005 |
| EP | 1 051 616 A2 | 11/2000 |
| EP | 1 484 601 A2 | 12/2004 |
| EP | 1 918 708 A2 | 5/2008 |
| EP | 1 718 973 B1 | 9/2009 |
| EP | 2 385 363 A2 | 11/2011 |
| FR | 2 929 407 A1 | 10/2009 |
| JP | H11-281645 A | 9/1999 |
| JP | H11-281645 A | 10/1999 |
| JP | 3496154 B2 | 2/2004 |
| JP | 2009-085839 A | 4/2009 |
| WO | WO 95/16207 A1 | 6/1995 |
| WO | WO 95/33996 A1 | 12/1995 |
| WO | WO 96/34287 A1 | 10/1996 |
| WO | WO 99/06827 A1 | 2/1999 |
| WO | WO 99/56111 A1 | 11/1999 |
| WO | WO 01/098783 A2 | 12/2001 |
| WO | WO 01/98783 A2 | 12/2001 |
| WO | WO 02/088739 A1 | 11/2002 |
| WO | WO 2004/003527 A1 | 1/2004 |
| WO | WO 2005/031355 A1 | 4/2005 |
| WO | WO 2005/075982 A2 | 8/2005 |
| WO | WO 2005/084534 A1 | 9/2005 |
| WO | WO 2005/111579 A1 | 11/2005 |
| WO | WO 2006/091631 A2 | 8/2006 |
| WO | WO 2006/099191 A2 | 9/2006 |
| WO | WO 2006/119203 A2 | 11/2006 |
| WO | WO 2006/129761 A1 | 12/2006 |
| WO | WO 2007/132375 A1 | 11/2007 |
| WO | WO 2007/132376 A2 | 11/2007 |
| WO | WO 2008/001279 A2 | 1/2008 |
| WO | WO 2010/015843 A1 | 2/2010 |
| WO | WO 2010/055308 A1 | 5/2010 |
| WO | WO 2010/148252 A1 | 12/2010 |
| WO | WO 2011/091473 A1 | 8/2011 |
| WO | WO 2011/154918 A2 | 12/2011 |
| WO | WO 2012/010454 A1 | 1/2012 |
| WO | WO 2012/044530 A1 | 4/2012 |
| WO | WO 2013/036913 A1 | 3/2013 |
| WO | WO 2014/085926 A1 | 6/2014 |

OTHER PUBLICATIONS

U.S. Appl. No. 14/431,155, filed Mar. 25, 2015, Parsons.
U.S. Appl. No. 14/672,789, filed Mar. 30, 2015, Parsons.
PCT/AU2013/001115, Dec. 17, 2013, International Search Report and Written Opinion.
AU 2013204428, Jan. 20, 2016, Patent Examination Report No. 2.
Extended European Search Report for European Application No. 14783290.1 dated Sep. 15, 2016.
Cook et al., Printed Circuit Board Tracking with RFID: Speed, Efficiency and Productivity Made Simple. Texas Instruments RFID White Paper. Feb. 2008; 9 pages.
Snyder, Diagnostic Considerations in the Measurement of Human Chorionic Gonadotropin in Aging Women. Clinical Chemistry. Aug. 11, 2005; 51(10):1830-35.
International Search Report and Written Opinion for Application No. PCT/AU2013/001115 dated Dec. 17, 2013.
Patent Examination Report No. 2 for Australian Patent application No. 2013204428, dated Jan. 20, 2016 (7pgs.).
Adejuwon et al., Daily serum choriogonadotropin concentrations in early human gestation. Int J Gynaecol Obstet. Apr. 1984;22(2):125-9.
Cole et al., Background hCG in non-pregnant individuals: Need for more sensitive point-of-care and over-the-counter pregnancy tests. Clinical Biochemistry. Feb. 2009;42(3): 168-75. doi: 10.1016/j.clinbiochem.2008.09.107. Epub Oct. 2, 2008. PubMed PMID: 18929550.
Cole et al., Normal production of human chorionic gonadotropin in perimenopausal and menopausal women and after oophorectomy. Int J Gynecol Cancer. Dec. 2009;19(9):1556-9.
Cole et al., Production of human chorionic gonadotropin during the normal menstrual cycle. J Reprod Med. Apr. 2009;54(4):245-50.
Corker et al., Hormonal patterns in conceptual cycles and early pregnancy. Br J Obstet Gynaecol. Jun. 1976;83(6):489-94.
Gronowksi et al., Use of serum FSH to identify perimenopausal women with pituitary hCG. Clin Chem. Apr. 2008;54(4):652-6. doi: 10.1373/clinchem.2007.100305. Epub Feb. 7, 2008.
Jia et al., Luminescence luteinizing hormone/choriogonadotropin (LH/CG) bioassay: measurement of serum bioactive LH/CG during early pregnancy in human and macaque. Biol Reprod. Dec. 1993;49(6):1310-6.
Mishell et al., Hormone patterns in early human gestation. Basic Life Sci. 1974;4(Pt. B):371-84.
Mishell et al., Serum gonadotropin and steroid patterns in early human gestation. Am J Obstet Gynecol. Nov. 1, 1973;117(5):631-42.
Rowe et al., An array immunosensor for simultaneous detection of clinical analytes. Anal Chem. Jan. 15, 1999;71(2):433-9.
Wide, Early diagnosis of pregnancy. Lancet. Oct. 25, 1969;2(7626):863-4.
Young et al, Development of an Ultrarapid One-Step Fluorescence Immunochromatographic Assay System for the Quantification of Microcystins, Environ. Sci. Technol. 2003, 37, 1899-1904.
Liu et al, Disposable Electrochemical Immunosensor Diagnosis Device Based on Nanoparticle Probe and Immunochromatographic Strip, Anal. Chem. 2007, 79, 7644-7653.
International Search Report and Written Opinion for International Application No. PCT/AU2011/000085, dated May 18, 2011 (16 pages).
Extended European Search Report dated Nov. 15, 2017 in connection with European Application No. 11736538.7.

* cited by examiner

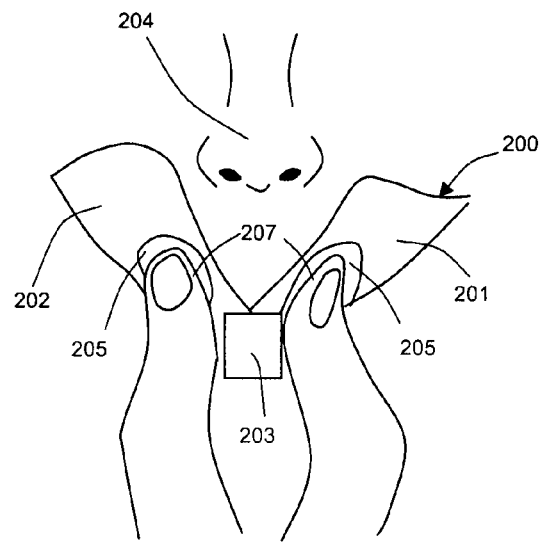
Fig. 8
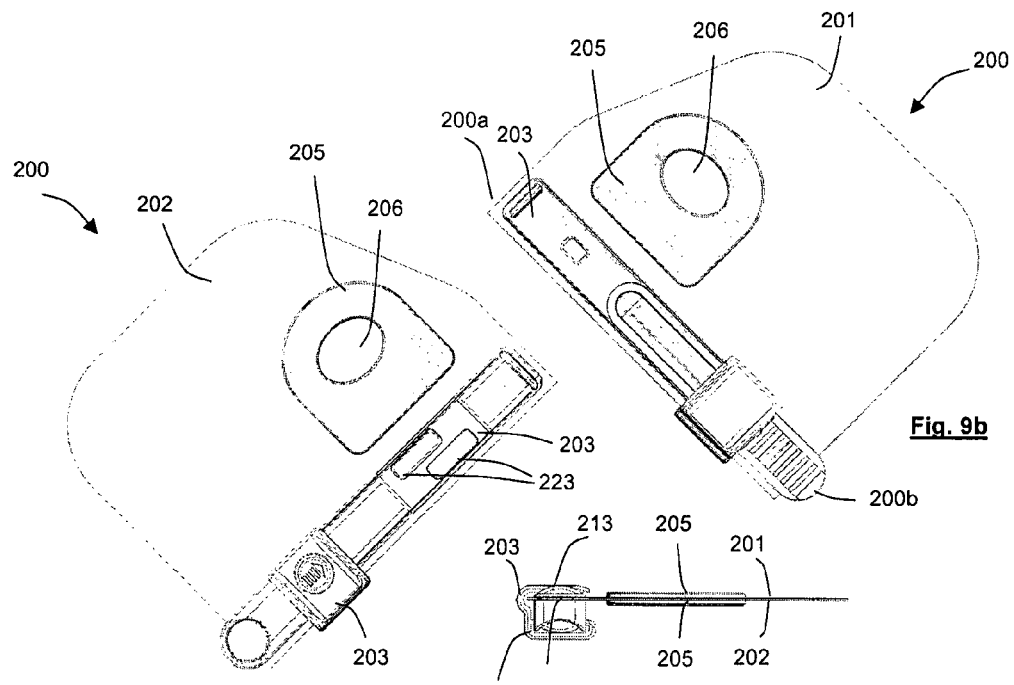
Fig. 9a
Fig. 9b
Fig. 9c

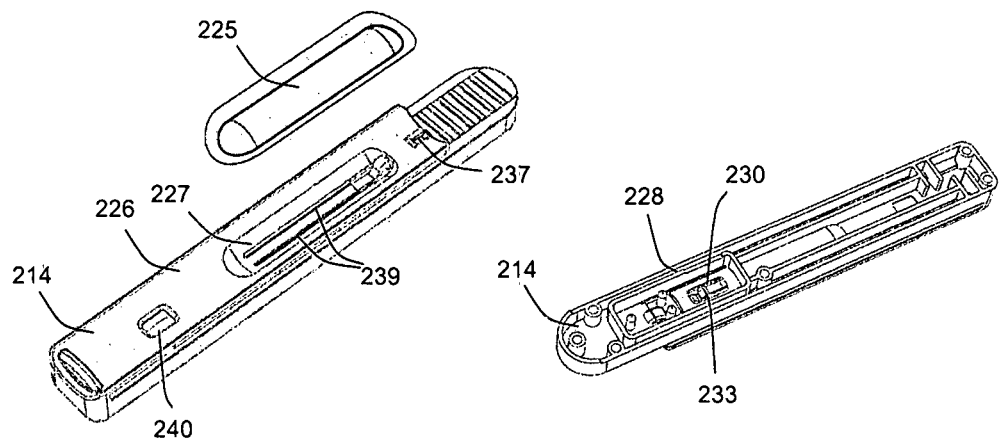
Fig. 11a     Fig. 11b
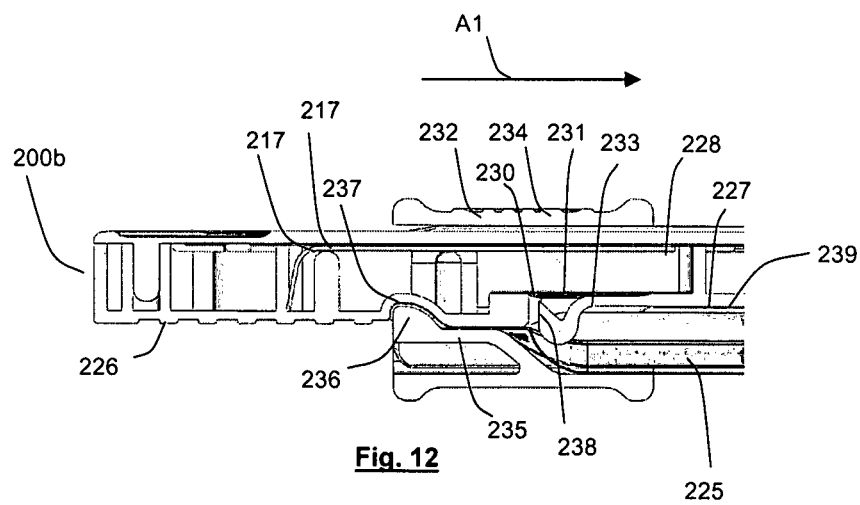
Fig. 12

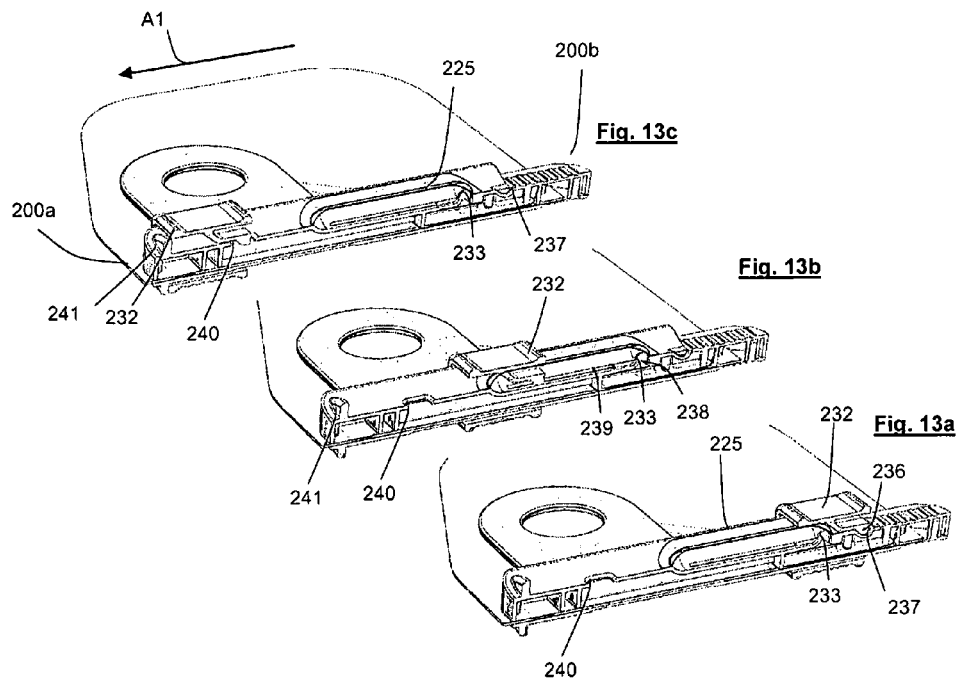
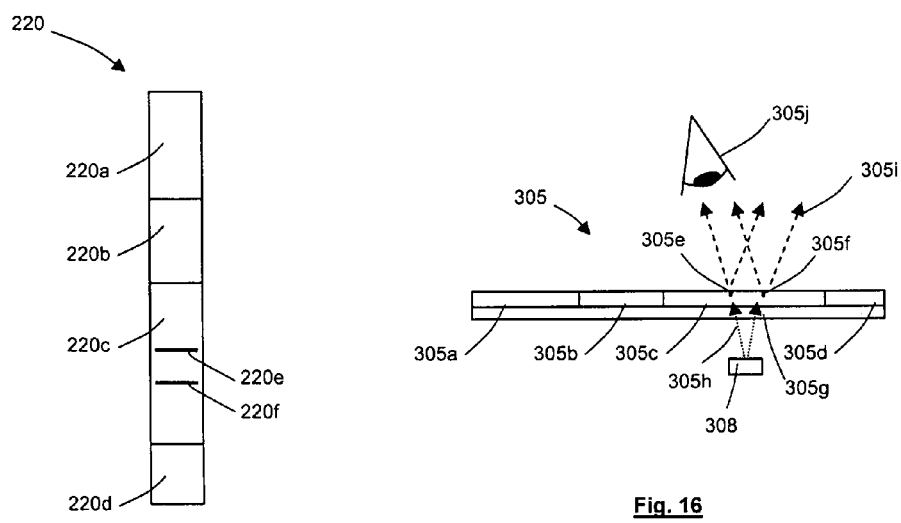

SAMPLING AND TESTING DEVICE FOR THE HUMAN OR ANIMAL BODY

RELATED CASE INFORMATION

This application is a 35 U.S.C. 371 U.S. National Stage Application of International Application No. PCT/AU2011/000085, filed on Jan. 27, 2011, claiming priority to Australian Application No. 2010900329, filed on Jan. 28, 2010, Australian Application No. 2010900557, filed on Feb. 11, 2010, and Australian Application No. 2010902158, filed May 18, 2010, the entire disclosures of which are incorporated herein by reference.

FIELD

The field of the invention relates to devices and methods for determination of the presence or absence of a biological entity in a human or animal body.

BACKGROUND

Immunochromatography is a well established testing method used to test for the presence or absence of an antigen (usually a biological protein) in a biological sample. The sample is supplied to a lateral flow test device and flows by capillary action through a label-holding substance which contains a soluble and labelled antibody specific to a particular antigen. If that antigen is present in the sample, an antigen-antibody (labelled) complex is formed which then continues to permeate by capillary action through the device to a test site where the complex is captured by a second antibody attached to the test site. This results in an increase in the density of captured antigen-antibody (labelled) complexes at the test site which results in a visible mark (usually a line) on the test site indicating the presence of the antigen in the sample.

Prior to carrying out the lateral flow test, the test sample must be obtained. This is often an invasive process, particularly if the fluid sample comprises nasal discharge, for example, requiring insertion of a foreign object into a body cavity to obtain the sample.

To obtain nasal discharge (e.g., mucus), a 'nasopharyngeal aspirate' is routinely performed, which involves passing a thin plastic tube into the nose and suctioning discharge from within the nose. Alternatively, a 'Q-tip' or 'cotton bud' is inserted via the nose into the nasopharynx and then withdrawn with a small sample of discharge. These methods are at present widespread in sampling nasal discharge for testing and are not without risks, including trauma to the nasopharyngeal mucosa and potential injury to the cribriform plate which forms the roof of the nose, separating it from the brain. Additionally, the accuracy of these test methods are highly dependent upon attaining a quality sample and therefore the skill of the person acquiring the sample. As a result these methods are carried out by trained health personnel and the associated devices are not necessarily available for sale direct to the public.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

According to a first aspect, the present invention provides a device comprising:
a sampling portion, the sampling portion comprising flexible material adjustably conformable to a part of a human or animal body for receiving a biological sample directly from the body; and
a test portion in fluid engagement with the sampling portion, the test portion comprising one or more test zones,
wherein the sampling portion and test portion are configured such that at least a portion of the sample received by the sampling portion is transferable to the test portion such as to contact one or more of the test zones, and wherein each test zone is configured to indicate the presence or absence of one or more biological entities in the sample.

According to a second aspect, the present invention provides a method for determination of the presence or absence of a biological entity in a human or animal body using a device comprising:
a sampling portion, the sampling portion comprising flexible material adjustably conformable to a part of a human or animal body for receiving a biological sample directly from the body; and
a test portion in fluid engagement with the sampling portion, the test portion comprising one or more test zones,
wherein the sampling portion and test portion are configured such that at least a portion of the sample received by the sampling portion is transferable to the test portion such as to contact one or more of the test zones, and wherein each test zone is configured to indicate the presence or absence of one or more biological entities in the sample,
the method comprising:
conforming the flexible material of the sampling portion to a part of the human or animal body;
depositing a biological sample on the sampling portion; and
observing a reaction at one or more of the test zones to the presence or absence of one or more biological entities in the sample.

The device and method may detect the presence or absence of one or more specific biological entities, such as antigens. The antigens may be found in common respiratory viruses including but not limited to Influenza A (including the H1N1 virus subtype), Influenza B, Respiratory Synctial Virus, parainfluenza viruses, adenoviruses, rhinoviruses, cornaviruses, coxsackie viruses, HIV viruses and/or enteroviruses. The device may also detect specific biological antigens found in bacteria, fungi, protozoa, Helminths, Mycoplasma and prions. The device may also be capable of detecting specific proteins produced by the human or animal body, including but not limited to immunoglobulin, hormone molecules, inflammatory or malignant proteins. The device may comprise a plurality of different test zones so that the presence or absence of different biological entities such as antigens can be tested simultaneously.

The device and method may permit identification of one or more biological entities using existing principles of lateral flow immunochromatography or other techniques. However, by combing the sampling portion and test portion in a single device, the device may provide a simple and low cost means for carrying out this process. The sampling portion and test portion may be combined in the device such that fluid engagement exists between the sampling portion and test portion prior to receipt of the sample and therefore, once the sample is deposited, the user may not need to perform any steps to bring the sampling portion and test portion into fluid engagement. For example, the user may not need to take hold of the test portion and move it into fluid engagement with the sample portion, which could otherwise complicate or adversely affect the testing procedure. In this specification, reference to the sampling portion and testing portion being "in fluid engagement" is intended to indicate the existence of a path between these two portions along which fluid can travel in a controlled manner. It is conceivable that a removable blocking element such as a release tab may be provided to obstruct the path, e.g. prior to testing. However, even with such a removable blocking element in place, the sampling portion and testing portion can still be considered in fluid engagement.

By providing flexible material adjustably conformable to a part of a human or animal body for receiving a biological sample directly from the body, which material may be at least partially absorbent, the device and method may provide a non-invasive, comfortable, intuitive and convenient means for obtaining and testing the sample. The sampling portion, or at least an absorbent portion thereof, can be configured to receive the sample directly from the body to the extent that no separate collection tool is needed to apply the sample to the sampling portion. Accordingly, collection of a sample using a swab or such like is not necessary, albeit this does not necessarily preclude the use of a separate collection tool with the device, should the user choose to use the device in that manner. The device and method may therefore provide a safe, quick and satisfactory alternative to invasive sampling. The device and method may encourage earlier and more frequent testing for the presence of biological entities in humans or animals. The device and method may be used to test for any biological entity placed directly onto the sampling portion by a method including, but not limited to, a typical 'nose blow'. The device and method may also allow testing for more than one biological entity at a time, either increasing the potential diagnosis of multiple organisms for example, or when used to test for the presence of different antigens from a single organism, increasing the diagnostic sensitivity.

The biological sample may be a fluid sample, or may be a substantially solid sample, which is transformed into a fluid upon application of a liquid such as a solution, e.g. a buffer solution, for example. The liquid may act as a carrier for the biological sample. The liquid may be applied to the sampling portion to increase the fluidity of the biological sample. This may be performed to facilitate or improve capillary transfer of the sample, whether the sample is initially solid or fluid, to test zones within the test portion. The liquid may be applied to the sampling portion of the device before or after receipt of the sample.

The liquid may be applied to the sampling portion by a variety of means. For example, the liquid may be applied using a dropper, such as a pipette, or drops may be applied from a squeezable bottle containing the liquid. Alternatively, the liquid may be provided in a reservoir that may be integral with the device. The reservoir may be a sealed reservoir containing the liquid and which is breakable and/or has a removable portion so that the liquid can be released. For example, the reservoir may take the form of a capsule, bubble or blister containing the liquid, or container having at least one thin wall, which is capable of breaking or bursting to release the liquid. The reservoir may have a weakened part to facilitate easier breaking or bursting of the reservoir, and this may be at a pre-determined position so that the liquid once released is distributed to an appropriate part of the device. An element maybe provided that is actuatable to break or burst the reservoir, which element may comprise a sharp point, for example. Preferably the reservoir is provided adjacent the sampling portion of the device. However, the reservoir may be provided at a variety of different positions of the device.

The flexible material of the sampling portion may be sufficiently supple to bend or fold freely or repeatedly in order to conform to a variety of different shapes of body parts. The flexible material may be bent or folded repeatedly without being substantially damaged, cosmetically and/or and functionally.

The flexible material may be conformable to the nasal region of the body, permitting a nasal discharge (e.g., mucus) sample to be provided directly to the sampling portion. The device may provide a means for testing a nasal discharge sample provided directly to the device via an act of nose blowing. The flexible material of the sampling portion may serve as a facial tissue or handkerchief. Additionally or alternatively, the flexible material may serve as a wipe, allowing a sample to be obtained by wiping or dabbing the flexible material across a portion of the body. The flexible material may be soft such as to prevent any substantial damage or pain to the body during the wiping, dabbing and/or nose blowing processes.

When used to test a nasal discharge sample, the flexible material may be sufficiently flexible to bend from contact portions adjacent the ala or alar groove of the nose, across the tip of the nose, for example. When used to test a stool sample, the flexible material may be sufficiently flexible to bend to a shape conforming to the intergluteal cleft, for example. In general, however, the flexible material may be conformable to any curved or angled parts of the body, such as parts of the legs, arms, feet, hands, face, head, back, torso and/or genitals, etc. The flexible material may be configured to receive, for testing, one or more of a variety of different types of samples directly from the body. Samples may include, for example, blood, serum, plasma, saliva, sputum, urine, ocular fluid, tears, semen, vaginal discharge, nasal secretions and droplets, ear secretions, perspiration, mucus, stool, and/or amniotic, spinal, wound, or abscess fluid.

In one embodiment, the device may be configured specifically for testing samples obtained from a respiratory system, such as secretions from the nose, nasopharynx, oral cavity, pharynx, and oropharynx. The secretions may include nasal mucus, droplets from coughing or sneezing, saliva, and pharyngeal and/or oropharyngeal fluid.

The flexible material may be at least partially absorbent material that can act as a lateral flow medium (e.g. capillary membrane) for transferring at least a portion of the sample from the sampling portion to the test portion. The flexible material may comprise or consist of one or more layers of material and/or padding.

The flexible material may comprise, for example, paper material and/or may be in the form of an absorbent pad. The paper material may be tissue paper or lightweight paper or medium weight paper or otherwise and the paper may be natural paper or synthetic paper. The flexible material may comprise, for example, non-woven rayon fabric or non-woven glass-fibre fabric. The flexible material may comprise polymer material and/or fibrous material such as wood pulp, woven or non-woven cellulose or nitrocellulose fabric.

The flexible material may comprise, for example, a cloth material, e.g. a woven or non-woven fabric material. The cloth material may comprise cotton, wool, polyester or acrylics, for example.

The material may be chosen to be flexible enough to conform to the appropriate body parts and soft enough to perform a wiping, dabbing or blow nose function without causing discomfort to the body being tested. The choice of material may be a balance between flexibility, softness, strength and ability to function as a lateral flow medium.

The sampling portion and test portion may form all or part of a test layer of the device. The sampling portion and testing portion may be integral with each other or may be two or more separate portions fixed together. The testing portion may comprise a flexible material, e.g. flexible material similar or identical to the flexible material of the sampling portion. The sampling portion and test portion may comprise the same material or different material. For example, the testing portion may comprise harder or more rigid material than the sampling portion, since it may not need to contact the body during the sampling process. One side only of the sampling portion or test layer may be designated as, or configured as, a target side, i.e., a side for contacting the body to receive the sample. The target side may comprise markings to indicate the appropriate position for body contact and deposition of the sample. Instructions for carrying out testing using the device and/or interpreting the test results, may also be provided, e.g. printed, on the sampling portion or other region of the test layer.

The device may comprise a cover layer. The cover layer may be attached to, and extend over, one side of the test layer, e.g., the target side of the test layer. A hole in the cover film may be provided so that an area of the sampling portion on that side of the test layer is exposed. Accordingly, a sample may be received by the sampling portion through the hole in the cover layer. The cover layer may be attached to, and extend over, all or part of one side of the test portion of the test layer.

In one embodiment, the plane of the test layer, the sampling portion may be provided at an inner region of the test layer and the test portion may be provided to the outside of the sampling portion. When a cover layer is provided, in the plane of the cover layer, the hole may be located at an inner region of the cover layer so that it aligns with at least a portion of the sampling portion.

The cover layer and hole therein may serve as a guide to ensure that a sample is applied directly to the sampling portion of the device and/or to a targeted area of the sampling portion. Furthermore, the cover layer may act as a barrier to prevent direct application of the sample, and/or other fluids or environmental substances, to the test portion, where it might come into contact with the one or more test zones and adversely affect test results. To ensure that a sample is applied to a targeted area of the sampling portion, particularly when the device is to be used to obtain a nasal sample through nose blowing, finger location guides may be provided. The arrangement may be such that a user will locate the device at the correct position with respect to the nose when their fingers are located in the guides, for example.

The cover layer may comprise fluid-resistant material. For example, the cover layer may comprise plastic material. The cover layer may be a flexible material (e.g. a flexible film) so that it does not prevent the flexible material of the sampling portion from being bent or manipulated into an appropriate shape to contact the body during the sampling process. All or part of the cover layer may be translucent or transparent so that a reaction between the sample and one of more of the test zones can be observed through the cover layer. Alternatively or additionally, the cover layer may comprise one or more windows arranged to align with the one or more of the test zones so that a reaction between the sample and the test zones can be observed through the windows of the cover layer. Instructions for carrying out testing using the device and/or interpreting the test results, may be provided, e.g., printed, on the cover layer.

The device may comprise a backing layer. The backing layer may be attached to, and extend over, one side of the test layer. The cover film may be provided on the opposite side of the test layer to the target side of the test layer. The backing layer may ensure that the sample received by the sampling portion does not leak from the sampling portion, e.g., onto a hand or other surface, and is instead directed toward the test portion of the test layer.

The backing layer may comprise fluid-resistant material. For example, the backing layer may comprise plastic material. The backing layer may be flexible material (e.g. a flexible film) so that it does not prevent the flexible material of the sampling portion from being bent or manipulated into an appropriate shape to contact the body during the sampling process. The backing layer may comprise slide resistant material, e.g., rubbery material, to allow easier gripping of the device by a person performing the testing. Furthermore, the slide resistant material may permit the device to grip to a surface (e.g. a table or bench top), whilst the reaction of the one or more test zones is observed. All or part of the backing layer may be translucent or transparent so that a reaction between the sample and one of more of the test zones can be observed through the backing layer. Alternatively or additionally, the backing layer may comprise one or more windows arranged to align with the one or more of the test zones so that a reaction between the sample and the test zones can be observed through the windows of the backing layer. Instructions for carrying out testing using the device and/or interpreting the test results, may be provided, e.g. printed, on the backing layer The device may comprise absorbent material to prevent fluid flowing through outer edges of the test layer and onto a users hand or the floor, etc. The absorbent material may be a strip of absorbent material located around the periphery of the device. The absorbent material may be integral to, or connected to, outer regions of one or more of the cover layer, test layer and backing layer. Alternatively, the absorbent material may be provided as an independent element of the device. For example, an additional layer comprising the absorbent material may be provided. The additional layer may extend beyond the outer edges of one or more of the cover layer, test layer and backing layer. The absorbent material may be more absorbent, e.g. have a greater fluid retention capacity, than the test layer.

The cover layer may extend to and align with outer edges of the test layer. As an alternative, the cover may extend only partway to the edges of the test layer. In the latter arrangement, an outer region, e.g. outer strip, of the test layer may be exposed beyond the outer edges of the cover layer. The outer region of the test layer may provide the aforementioned absorbent material to prevent fluid flowing through the outer edges of the test layer.

The device may be substantially flat. The device may be a cloth-like device. That is, the entire device may be a substantially flat, pliable element, easily handled and manipulated by a patient or other person carrying out the testing. The test layer, cover layer and/or backing layer may each comprise a single layer of material only or comprise multiple layers of material.

The device may be foldable such that, following deposition of a sample on the sampling portion, the sampling portion including the sample can be hidden from view. This may be desirable as a sample may be considered unsightly. Whilst the sample is visible, the user may be reluctant to pass the device to another person, e.g., a clinician, for analysis of test results. The device may be folded so that only the backing layer is visible, for example. The device may be foldable in half or other manner, to achieve the desired effect. The device may comprise one or more fold lines to indicate the appropriate position for folding.

If liquid, such as buffer solution, for increasing the fluidity of the biological sample, is provided in a reservoir in accordance with the preceding discussions, the reservoir may be configured to release the liquid upon folding of the device. For example, the reservoir may be configured to burst or break during or after folding of the device. The process of folding the device alone may be sufficient to cause the release of the liquid. Alternatively, release of the liquid may be achieved by further user intervention, such as the user applying force to the reservoir after folding, using their fingers for example. Alternatively, release of the liquid may be achieved by a combination of the folding process and the user applying additional force to the reservoir. The reservoir may be located across or adjacent a fold line of the device. Accordingly, once the device is folded, a user may have easier access to the reservoir as the reservoir may be located at the edge of the folded device. The reservoir may be folded upon folding of the device. This may allow a user to press opposite sides of the folded reservoir against one another to force the reservoir to release the liquid.

As an alternative, the device may be substantially pre-folded. For example, the device may take generally, a butterfly configuration. To this extent, the device may include two flexible wings at least partially forming the sampling portion, and a central housing (spine) located between the two wings. The wings may be relatively pivotable or flexible about the housing.

In general, whether or not the device takes a butterfly configuration, a housing may be provided in the device and arranged to at least partially enclose and/or protect one or more components of the device. For example, the housing may enclose at least partially the testing portion of the device, the liquid reservoir and/or other elements discussed herein. The housing may be substantially rigid and may prevent or reduce the likelihood of damage to the test portion, liquid reservoir and/or other elements enclosed therein. When the housing comprises the testing portion, the housing may include one or more openings or transparent portions to permit observation of the results of testing.

The device may comprise one or more lateral flow test strips, e.g. conventional lateral flow strips that are already available. The test strips may be Quickvue® influenza A and B test strips produced by Quidel Corporation, or BinaxNOW® influenza A and B test strips produced by Inverness Medical Innovations, Inc., for example. Each test strip may provide a respective test portion of the device. Each test strip may be incorporated into the device such as to be in fluid engagement with the sampling portion. The device may provide, in essence, an adapter for one or more conventional lateral flow test strips such as to allow convenient and comfortable deposition of a sample that can be transferred to the one of more test strips. The test strips may be located in a housing of the device. In one embodiment, the device may be configured to allow insertion of one or more lateral flow test strips into the device that have been selected by the user or manufacturer dependent on the desired testing to be carried out.

In one embodiment, an actuator mechanism may be provided to release liquid from the reservoir. The actuator mechanism may comprise, or interact with, a piercing element, such that, upon operation of the actuator mechanism, the piercing element may burst the reservoir, for example. The actuator mechanism may comprise an actuation element that is moveable, e.g., slidable or pivotable, relative to the sampling portion and/or the testing portion. The actuation element may have additional or alternative functions. For example, the actuator element may be configured to spread the sample, e.g., prior to causing release of the fluid from the reservoir. As another example, the actuator element may be configured to activate an LED, in accordance with subsequent discussions herein.

According to a third aspect, the present invention provides a device comprising:

a sampling portion for receiving a biological sample directly from the body;

a test portion in fluid engagement with the sampling portion, the test portion comprising one or more test zones; and a sealed reservoir containing liquid, wherein the sampling portion and test portion are configured such that at least a portion of the sample received by the sampling portion is transferable to the test portion such as to contact one or more of the test zones, and wherein each test zone is configured to indicate the presence or absence of one or more biological entities in the sample; and wherein the device is foldable and the sealed reservoir is configured such that, after or during folding, the liquid is releasable from the reservoir to increase the fluidity of the biological sample.

The device according to the third aspect may have any one or more features of the device described with respect to the first and second aspects of the invention. For example, the reservoir of the device may be a capsule, bubble or blister, where the liquid is released from the reservoir through a force applied to the reservoir upon folding and/or through the application of an additional force by the user after or during folding. As another example, the sampling portion may comprise flexible material adjustably conformable to a part of a human or animal body for receiving a biological sample directly from the body. Nonetheless, it is conceivable that the sampling portion in this third aspect may exhibit less flexibility and may receive a biological sample that is dropped onto the sampling portion, or applied to the sampling portion using a tool such as a dropper or device such as a cotton bud.

In any of the preceding aspects, the device may comprise one or more fixation devices to maintain the device in a folded configuration. The fixation devices may be releasable or non-releasable. The fixation devices may comprise hook and loop fasteners (Velcro™), clips, adhesive or otherwise. The fixation devices may be provided at edges and/or corners of the device for example. The fixation devices may be provided on any one or more of the cover layer, test layer and backing layer. If the device is square or rectangular in shape, for example, the fixation devices may be provided at or adjacent two corners of the device, and complimentary fixation devices may be provided at or adjacent the other two corners of the device such that, upon folding the device in half, the fixation devices will co-operate and fix to each other. If the fixation devices are e.g., adhesive, however, rather than fixation devices fixing to each other, the fixation devices may fix directly to another portion of the device, e.g., to one or more of the cover, test and backing layers of the device.

The device may be maintained in the folded configuration during observation of the test results. Observation may be made through one or more translucent or transparent portions of the backing layer or housing, or one or more windows provided in the backing layer or housing, for example.

The sampling portion of the device, configured to conform to the body to receive the sample, may have a minimum surface area of about 5 cm$^2$ or 10 cm$^2$ or 20 cm$^2$ or 30 cm$^2$ or 40 cm$^2$ or 50 cm$^2$ or 100 cm$^2$ and may have a minimum diameter, or length and/or width, of about 2 cm or 3 cm or 4 cm 5 cm or 6 cm or 7 cm or 10 cm.

The device, for example when configured as a cloth-like device, may have a minimum surface area on one side of about 100 cm$^2$ or 150 cm$^2$ or 200 cm$^2$ and may have a minimum diameter, or length and/or width, on one side of about 10 cm or 15 cm or 20 cm.

The test portion of the device may be provided with antigens or antibodies to allow testing for the presence of one or more biological entities using existing principles of lateral flow immunochromatography.

One or more label-holding areas, e.g. coloured label-holding areas containing specific antibodies bound to light visible molecules, may be provided in the test portion. The label-holding areas may be located at the edge or adjacent the edge of the test portion, at the boundary between the test portion and the sample portion. The sample received by the sample portion may travel via capillary action through the sample portion and into the test portion where it mixes with the label-holding areas and may form antigen-antibody (labelled) complexes.

The one or more test zones may be spaced from the boundary between the test portion and the sample portion. Accordingly, the sample may encounter the label-holding areas prior to reaching the test zones. The test zones may comprise stripes (lines), crosses, squares or other shaped regions of the test portion that have been impregnated with antibodies or antigens. Depending upon the biological antigens present in the sample, and the antibodies or antigens at the label-holding areas and the test zones, the sample may become bound at one or more of the test zones, causing a colour change at the test zones. The change in colour may therefore be indicative of the presence or absence of a specific biological entity in the sample, such as, but not limited to, influenza A or influenza B.

A plurality of test zones may be provided such that the presence or absence of a plurality of different types of biological entities in the sample may be tested. Any number of different test zones up to, for example, ten test zones may be provided. When the sampling portion is located at an inner region of the test layer and the testing portion is located to the outer side of the sampling portion, the test zones may be distributed radially about the sample portion, so that the sample, which may spread radially from the sample portion, may contact each test zone independently. In this instance, the label-holding areas may be provided across a region of the testing portion encircling the sample portion.

Although the device may use principles of immunochromatography, it is conceived, however, that alternative means of testing could be incorporated into the device.

The device may provide a rapid diagnosis test device, permitting testing in less than 1 minute or less than 10 minutes of less than 30 minutes or less than one hour, for example. The device may be disposable, configured for one-use only. The device may be provided in sterile packaging prior to use. The device may provide a means for entirely non-invasive testing for the presence or absence of one or more biological entities. The device may be used for testing in the veterinary field as well as in the field of human medicine.

In any of the aspects, upon indicating the presence of a biological entity, the device may be configured to display a code or identifier that is unique to the biological entity and/or the test device.

According to a fourth aspect, there is provided a device comprising:

a sampling portion for receiving a biological sample directly from the body; and a test portion in fluid engagement with the sampling portion, the test portion comprising one or more test zones;

wherein the sampling portion and test portion are configured such that at least a portion of the sample received by the sampling portion is transferable to the test portion such as to contact one or more of the test zones, and wherein each test zone is configured to indicate the presence or absence of one or more biological entities in the sample; and wherein, upon indicating the presence of a biological entity, the device is configured to display a code or identifier that is unique to the biological entity and/or the test device.

The device of the fourth aspect may be used to verify a positive test for a biological entity in the sample.

According to a fifth aspect, there is provided a method for verifying a positive test for a biological entity in a biological sample comprising:

testing for the presence of the biological entity using a test device wherein, upon determining the presence of a biological entity in the biological sample, the test device displays a code or identifier that is unique to the biological entity and/or the test device; and submitting the code or identifier to a health service.

The device employed in the method of the fifth aspect may be a device according to any one of the preceding aspects.

In the devices of any of the previous aspects, the test zones of the device may display an indicator, e.g. a symbol, to indicate a positive or a negative test result (i.e. to indicate the presence or absence of a specific biological entity in the sample), such as a "+" or a "−" respectively. However, in line with the preceding discussion, the test zones may additionally or alternatively display a unique code or identifier indicative of a positive test result. The code or identifier (referred to hereinafter as "the code") may be unique to the biological entity present in the sample and/or unique to the device through which the testing is performed. The code may be alphanumeric. Normally the code may be invisible to the user, but may appear when an element defining the code, such as a region of the test portion that has been impregnated with antibodies or antigens, comes into contact with the specific biological entity that is being tested.

Once the code or identifier is obtained, or "revealed" by the test device, it may be provided to a third party, such as a health service. The health service may be a pharmacy, doctor's surgery, hospital, national health service or otherwise. The code may be provided to the service through a website interface, via phone, email, "SMS" or otherwise. Once the code has been provided, the code may be checked by the service against a database of codes to determine whether the code is a valid code, and/or to determine a biological entity associated with the code. Alternatively, the code may comprise descriptive elements that can be directly decoded by the service to determine the validity of the code and/or a biological entity associated with the code. The processing of the code may be automated, e.g. using a computer database and/or processor.

By providing the code to the health service, a number of consequences may be achievable. For example, the code may allow national health statistics to be recorded and prevent people from recording false instances of, for example, influenza. The code may allow for accurate and proper dispensing of appropriate medication to a person presenting the code, e.g., through automated means such as an e-pharmacy. This may have particular advantages during a pandemic. The code may ensure that a legitimate request for medication is being made.

Although the code may be revealed automatically when a positive test result is obtained, as an alternative, the code may be revealed by removing, e.g., peeling back, a portion of the device under which the code may be displayed, for example. The portion that is removed may be a tab of the cover layer or backing layer of the device, for example. As an alternative, or additionally, the device may comprise a digital reader, which displays the code via a digital output means such as an LCD or LED screen.

The device may carry advertising, printed on its cover layer and/or backing layer, for example, which advertising may relate to remedies to cure any ailment for which the user may test positive using the device.

In some embodiments, the device may comprise a light source configured to enhance the readability and clarity of test results. The light source may be configured to operate at a precise frequency suitable for enhancing the indicator of a positive and/or negative result at the one or more test zones (e.g. a line or cross, etc.). The light source may comprise one or more light emitting diodes (LEDs), for example.

The light source may provide enhancements in accordance with principles of fluorescence discussed in European Patent Publication No. EP 1582598 A1, the contents of which are incorporated herein by reference. Accordingly, in a device according to the present invention, a persistent fluorescent structure may be provided in the label-holding zone and the arrangement may be such that the fluorescent structure, which may be one or more quantum dots, for example, can bind at the label-holding zone to the biological entity (target analyte) under test, and can be retained as part of a labelled complex at the test zone. The light source may be configured to emit a wavelength of light suitable for causing fluorescence of the fluorescent structure, causing the structure when present at the test zone to fluoresce and emit fluorescent light at a different wavelength to the light source. In effect, when a target analyte is present in the sample, the indicator at the test zone may fluoresce, increasing the ease at which the indicator can be read, whether visually (e.g., if the fluorescent light is in the visible wavelength range), or using an additional device such as an electronic reader. An electronic reader may include one or more photodiodes or other photoelectrical devices. The fluorescence may increase substantially the effective sensitivity of the device, which may be dictated by the user's ability to observe an indicator at the one or more test zones or the sensitivity of an electronic reader.

In accordance with one or more aspects of the present invention, however, the light source may be configured to backlight the one or more test zones of the testing portion. Accordingly, the light source may not obscure a user's line of sight of the test zones, or a path for the fluorescent light to be transmitted to an electronic reader. To enable backlighting of the test zones, the test portion may be partially or entirely transparent or translucent.

The light source may be actuatable by way of an actuation mechanism that also releases liquid from the one or more reservoirs that may optionally be comprised in the device, as discussed above. Accordingly, the illumination means may remain off at least until the user releases liquid held in the one or more reservoirs. Additionally or alternatively, the light source may be actuatable automatically upon sensing liquid. For example, the light source may be actuatable automatically upon a liquid sample (e.g. blood or urine) being deposited or transferred to the sampling portion or testing portion and/or upon sensing of liquid from a reservoir, which may be included in the device, at the sampling portion or testing portion. To actuate the light source, the device may comprise an electronic circuit that is connected to spaced points of an absorbent part of the sampling and/or testing portion, such that liquid passing through the absorbent part will complete the electronic circuit.

This approach to illuminating the testing portion to enhance the readability of the test results may be carried out with respect to the device according to any one of the preceding aspects, e.g. a device configured to test for the presence or absence of one or more biological entities in a biological sample, the device including a sampling portion comprising flexible material adjustably conformable to a part of a human or animal body for receiving a biological sample directly from the body; and a test portion in fluid engagement with the sampling portion, the test portion comprising one or more test zones.

However, in accordance with the sixth aspect of the present invention discussed below, the approach may also be taken with other test devices, which devices may not comprise a sampling portion that has the same flexibility properties, for example. The approach may be applied to otherwise conventional pregnancy test kits or virus test kits, for example.

According to a sixth aspect, the present invention provides a device configured to test for the presence or absence of one or more biological entities in a biological sample, the device comprising:

an at least partially transparent or translucent medium, the medium comprising:
    a label-holding zone including a labelling substance configured to bind a fluorescent structure to a biological entity in the biological sample; and
    a test zone configured to indicate the presence or absence of one or more biological entities in the sample, and
a light source;
wherein the test zone is readable at a first surface of the medium, and the light source is located adjacent a second surface of the medium, at a substantially opposing side of the medium to the first surface, such as to backlight the test zone.

The medium may be a planar structure. The medium may be a lateral flow medium. For example, the medium may be a sheet or strip of material. The medium may be a lateral flow test strip, for example.

BRIEF DESCRIPTION OF THE DRAWINGS

By way of example only, embodiments are now described with reference to the accompanying drawings, in which:

FIG. 8 shows a schematic oblique view of a device according to a fifth embodiment of the present invention;

FIGS. 9a and 9b show opposing side views of the device of FIG. 8, and FIG. 9c shows an end view of the device of FIG. 8;

FIGS. 11a and 11b show bottom and top views respectively of a spine of the device of FIG. 8;

FIG. 12 shows a partial cross-sectional view of the spine of the device of FIG. 8;

FIGS. 13a to 13c show oblique cross-sectional views of the device of FIG. 8 with a slider in different actuation positions;

FIG. 14 shows a schematic plan view of a test strip for use in the device of FIG. 8;

FIG. 16 shows a schematic side view of a test strip and LED for use in the device of FIG. 15.

DETAILED DESCRIPTION OF EMBODIMENTS

Figure 1:
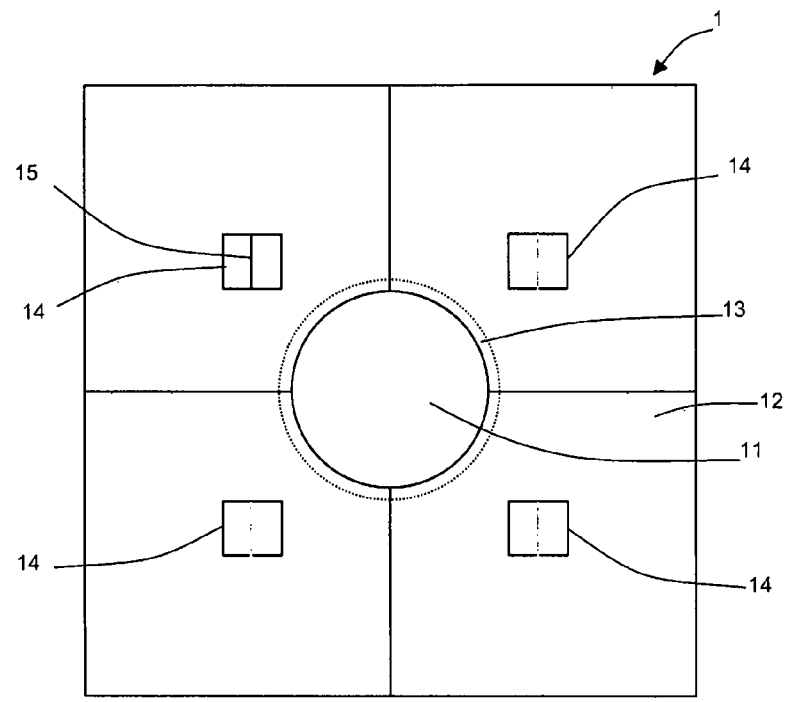
FIG. 1 shows a plan view of a test layer of a device according to a first embodiment of the present invention.

A test layer 1 for a device 10 according to a first embodiment of the present invention is shown in FIG. 1. The test layer 1 is a substantially square, pliable sheet, formed of soft, absorbent padding material. The test layer 1 is divided into two sections: a sampling portion 11, provided at a central region of the test layer 10; and a testing portion 12, provided to the outer side of the sampling portion 11. The testing portion 12 is formed integrally with the sampling portion 11 in this embodiment. The sampling portion 11 is designed to have a sufficiently large surface area, and to be sufficiently pliable, to extend over a person's nose, permitting the person to deposit nasal mucus on the sampling portion 11, using a standard nose blowing technique.

The testing portion 12 comprises a label-holding zone 13 encircling the boundary between the testing portion 12 and the sampling portion 11 and formed of a strip of the testing portion impregnated with a label-holding substance which contains a soluble and labelled antibody specific to a particular antigen. The testing portion 12 further comprises four test zones 14, each provided to the outer side of and spaced from, the label-holding zone. Each test zone comprises a short thin test line 15, which is a line on the surface of the testing portion impregnated with antibodies or antigens.

In use of the device 1; after a nasal mucus sample is deposited at the sampling portion 11, a buffer solution is dropped onto the mucus sample, using a dropper, increasing its fluidity. The sample spreads out from the deposition point, through the testing layer 1, via capillary action. Upon crossing the boundary between the sampling portion 11 and the testing portion 12, depending on the type of antigens present in the sample, the sample can combine with the labelled antibodies at the label-holding zone 13 to form an antigen-antibody (labelled) complex. Upon continued movement through the testing portion, the complex can encounter the test zones 14, causing a colour change along one or more of the test lines 15. The change in colour can thus be indicative of the presence of a specific biological antigen in the sample. By providing four different test zones 14, in this embodiment the presence or absence of at least four different biological antigens may be detected.

Figure 2:
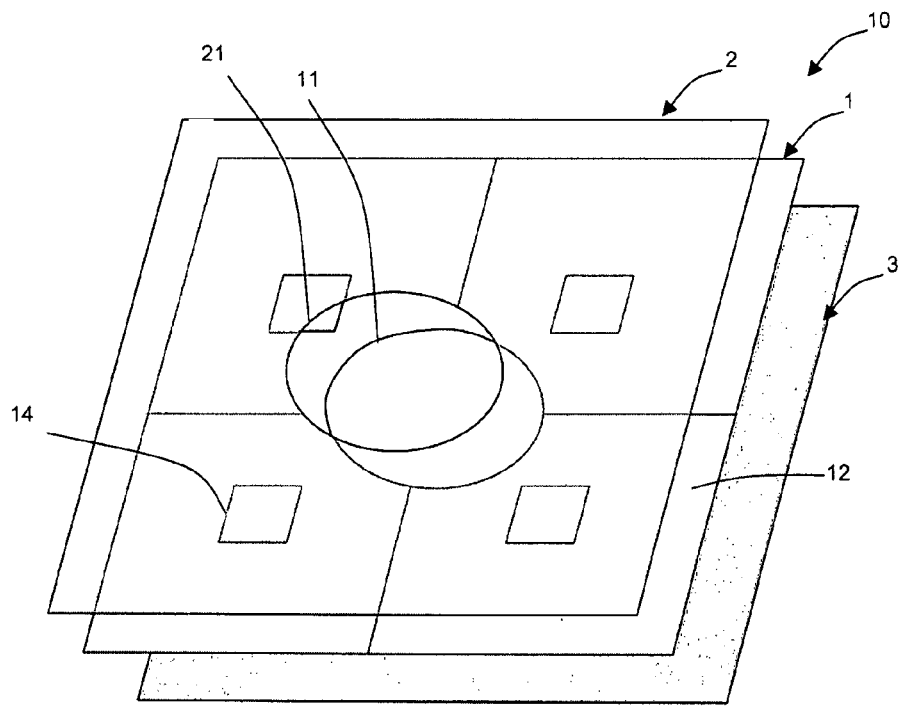
FIG. 2 shows an exploded view of a device according to the first embodiment of the present invention, comprising the test layer of FIG. 1.

With reference to FIG. 2, in addition to the test layer 1, the device 10 comprises a cover layer 2 and a backing layer 3. The cover layer 2 is a transparent, flexible film of fluid-resistant plastic material attached to a front side of the test layer 1. The cover layer 2 extends to the outer edges of the testing layer 1, but a hole 21 is provided at the centre of the cover layer 2, aligned with the sampling portion 11 of the test layer 1. Accordingly, a fluid sample can be received by the sampling portion 11 through the hole 21 in the cover layer 2. The cover layer 2, and hole 21 thereof, are arranged to serve as a guide, indicating where the fluid sample should be deposited, and the cover layer is also arranged to act as a barrier to prevent direct application of the fluid sample, and/or other fluids or environmental substances, to the test portion 12, which might adversely affect test results. Furthermore, the cover layer 2 can prevent leakage of the fluid sample through the front of the test layer 1. Since the cover layer 2 is transparent, the reactions at the test zones 14 can be observed through the cover layer.

The backing layer 3 is attached to the rear side of the test layer 1 and extends to the outer edges of the test layer 1. The backing layer 3 comprises flexible, fluid-resistant material, which prevents leakage of the fluid sample through the rear of the device, e.g., onto a hand or other surface. The material of the backing layer 3 is preferably slide resistant material to allow easier gripping of the device by a user, and to facilitate gripping of the device onto a surface (e.g. a table or bench top), whilst the reaction of the one or more test zones 14 is observed.

Figure 3:
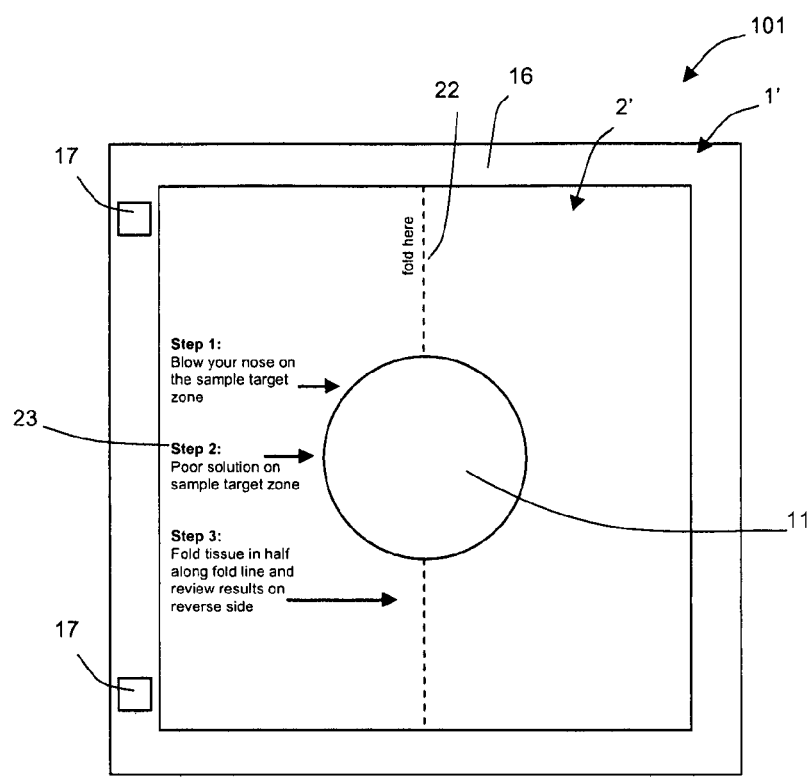
FIG. 3 shows a front plan view of a device according to a second embodiment of the present invention.
Figure 4:
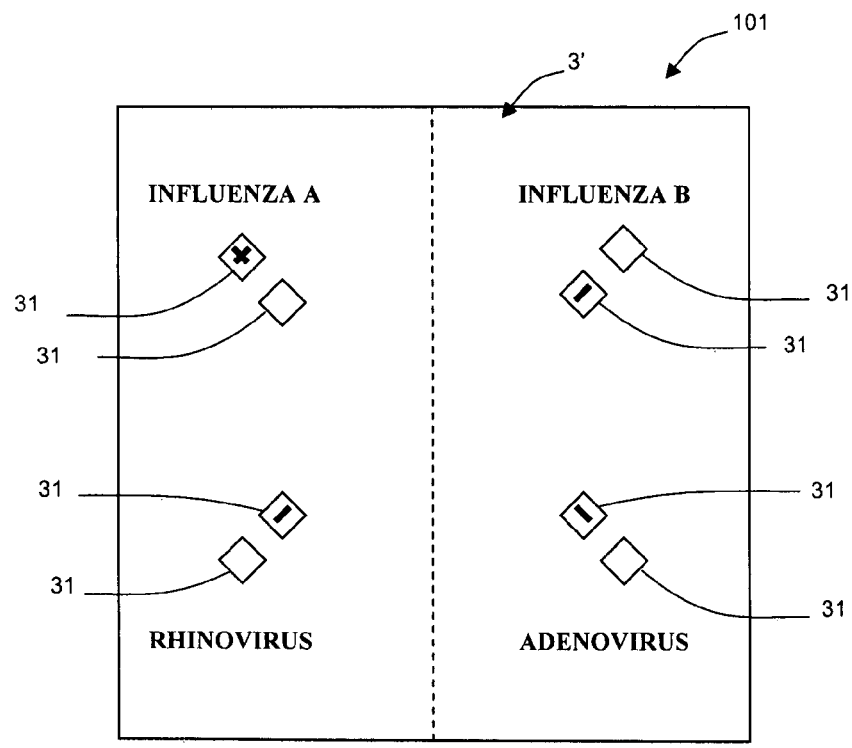
FIG. 4 shows a rear plan view of the device of FIG. 3.

A device 101 according to a second embodiment of the invention is shown in FIGS. 3 and 4. The device 101 is similar to the device 10 of the first embodiment. However, the cover layer 2' of the device 101 does not extend to the edges of the test layer 1'. Rather, it stops short of the edges of the test layer 1', leaving an outer region of the front surface of the test layer 1' exposed. In this embodiment, the exposed outer region of the test layer 1' is an absorbent strip of material 16. The absorbent strip 16 is formed of a different material to the remainder of the test layer 1'. Particularly, the material of the absorbent strip 16 is more absorbent than the remainder of the test layer 1'. Accordingly, the absorbent strip 16 can prevent fluid from spilling out of the edges of the test layer 1' onto a user's hands or the floor etc.

Furthermore, the device 101 comprises two fixation devices, in particular two adhesive pads 17, located proximate two adjacent corners of the test layer 1'. The adhesive pads 17 are arranged to stick, upon folding of the device 101 in half, to locations proximate the other two corners of the test layer 1'. To help a user fold the device in half, a dotted fold line 22 is printed down the centre of the cover layer 2'. In alternative embodiments, a cut or channel may also be provided in one or more of the layers of the device 101 to assist folding. The device 101 is arranged to be folded after deposition of a sample on the sampling portion 11 such that the sample is no longer visible. Instead, only the backing layer 3' will generally be visible after folding. Following on from this, with reference to FIG. 4, observation of test results using the device 101 can be made through the backing layer 3' in this embodiment. Particularly, the backing layer 3' comprises windows 31 through which the reaction of the test zones can be observed. More particularly, the backing layer 3' comprises four sets of two windows 31, the two windows of each set allowing observation of a positive or negative indication at each test zone for the presence of various virus antigens in the sample under test. In this embodiment, markings are printed on the backing layer 3' to indicate different types of viruses that are under test. Other markings such as brief instructions 23 and guidance on interpretation of results and/or a direction to refer to an instruction book, a handbook and/or an associated website, can also be provided on the backing layer 3'.

Figure 5:
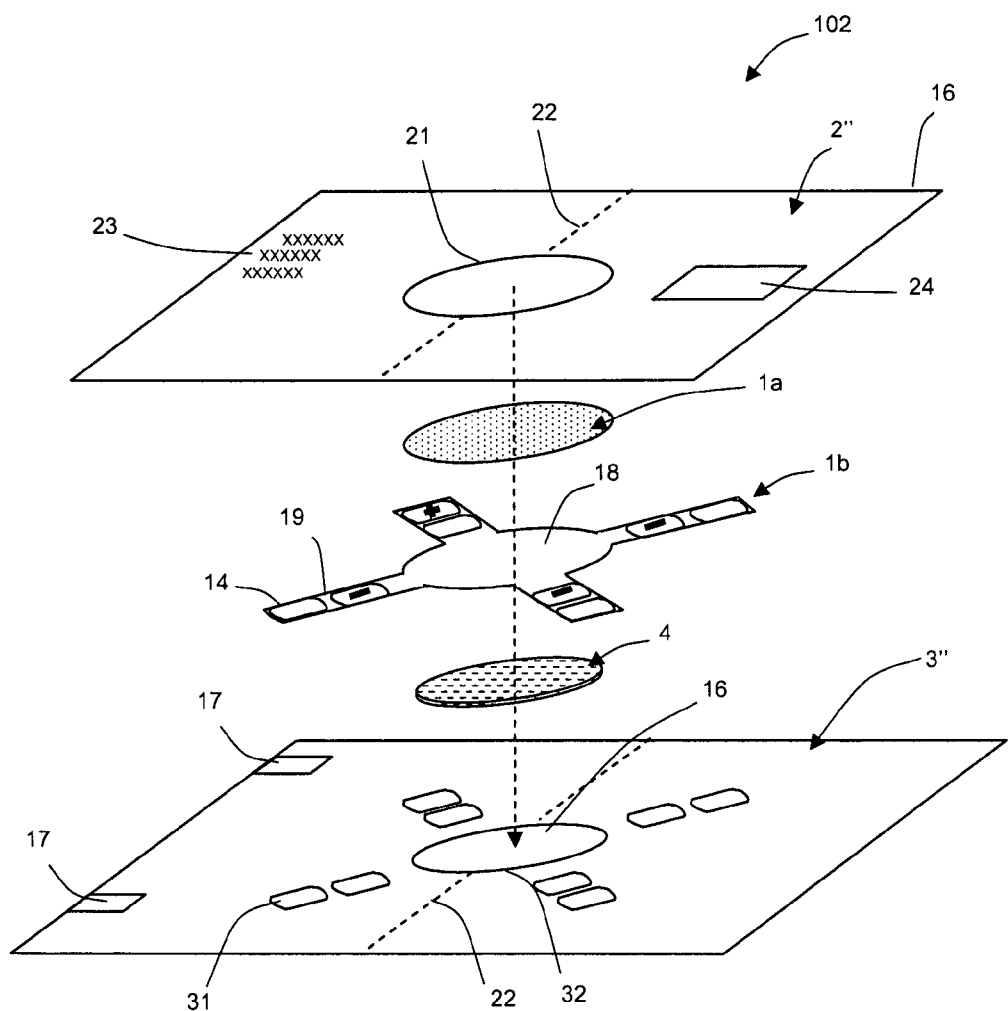
FIG. 5 shows an exploded view of a device according to a third embodiment of the present invention.

A device 102 according to a third embodiment is shown in FIG. 5. In this embodiment the test layer is made up of two separate layers, a sampling layer 1*a*, which is a substantially circular pad that is arranged to locate underneath a central hole 21 in the cover layer 2", and a test strip layer 1*b*, which has a central substantially circular section 18 that is arranged to locate underneath both the hole 21 and the sampling layer 1*a*, and also has four arms 19 projecting radially from the central section 18. The sampling layer 1*a* in combination with the central section 18 of the test strip layer 1*b* provide at least part of a sampling portion for the device 102, for receiving a sample from a patient through the hole 21 in the cover layer 2", and the arms 19 of the test strip layer 1*b* provide at least part of a test portion for the device 102.

At the transition between the central section 18 and the arms 19 of the test strip layer 1*b*, a label-holding zone is provided which is configured substantially as described above with respect to previous embodiments. The testing layer 1*b* further comprises a plurality of test zones 14, each provided on one of the arms 19 extending from the central section 18. The test zones 14 are also configured substantially as described with respect to previous embodiments. By providing four different test zones 14 in this embodiment, the presence or absence of at least four different biological antigens may be detected.

The device 102 also comprises a sealed reservoir of buffer solution, taking the form of a substantially circular, low profile capsule 4 in this embodiment. The capsule 4 is provided underneath the sampling layer 1*a* and the central section of the test strip layer 1*b*. A backing layer 3" is also provided to the underside of the test layer, but which has a central substantially circular window 32 in which the capsule 4 can locate. The capsule 4 is provided across a central fold line 22 of the device.

Figure 6:
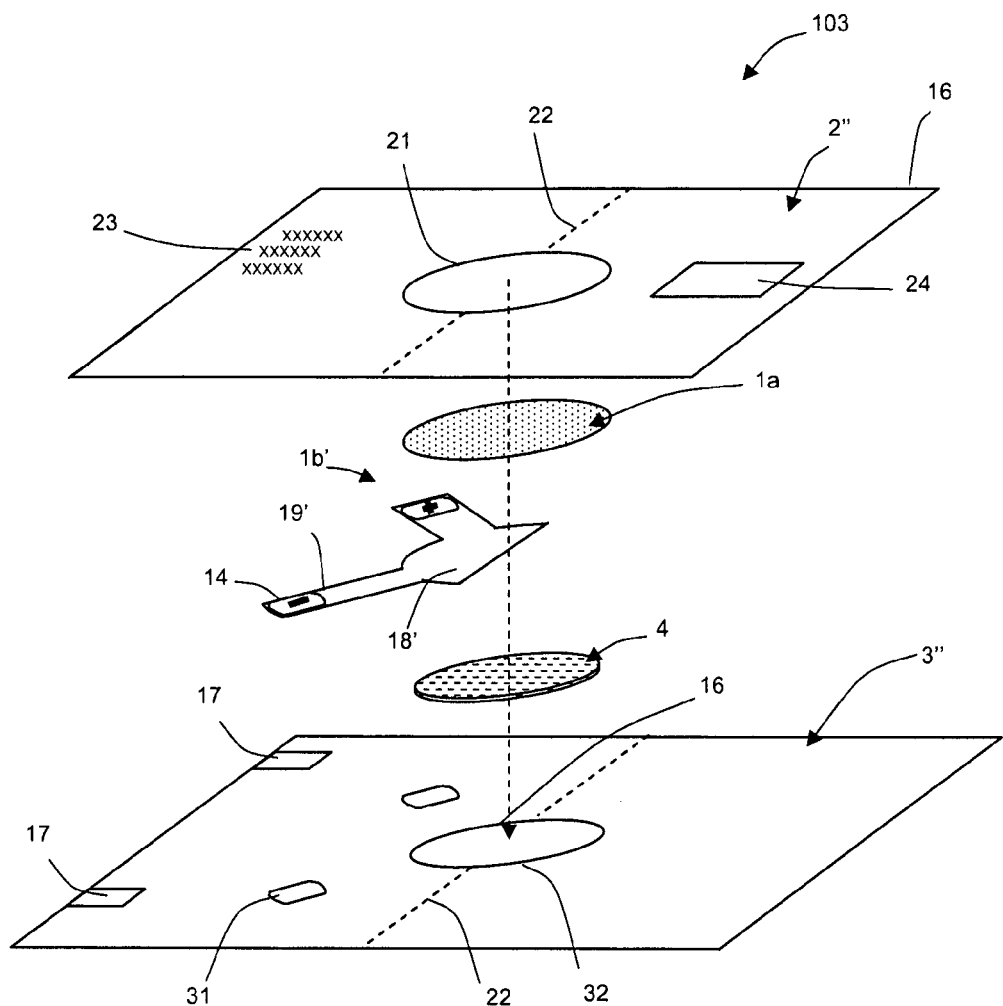
FIG. 6 shows an exploded view of a device according to a fourth embodiment of the present invention.

A device 103 according to a fourth embodiment is shown in FIG. 6. The device is substantially the same as the device of FIG. 5. However, the test-strip layer 1*b'* has been, effectively, cut in half. In this regard, it comprises a substantially semi-circular central section 18' and comprises only two arms 19', allowing determination of the presence or absence of two different biological entities. The central section 18' and arms 19' are provided to one side only of the fold line 22 of the device. Accordingly, the central section does not interfere with folding of the device, and observation of the test results on one half only of the backing layer need be made, when the device is used in a manner described below.

Figure 7A:
FIGS. 7a to 7d show steps for using the device of FIG. 6.
Figure 7B:
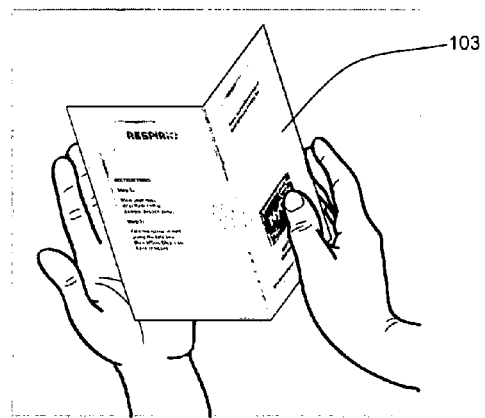
Figure 7C:
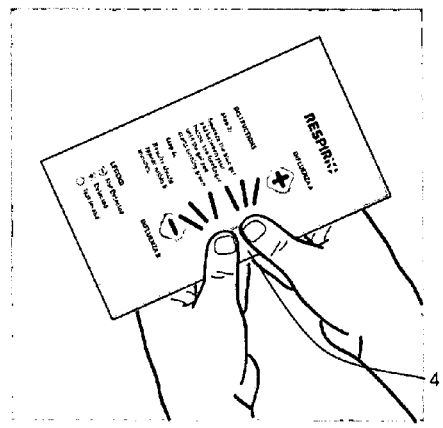
Figure 7D:
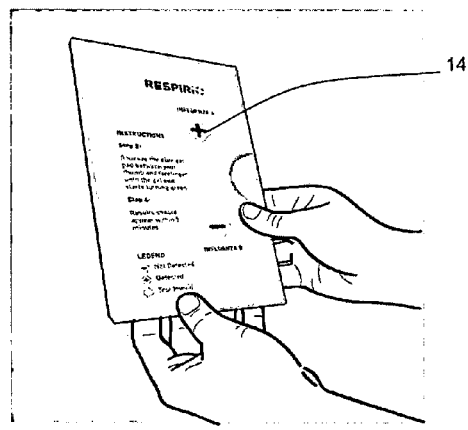

With reference to FIGS. 7*a* to 7*d*, a method of using the device of FIG. 5 or 6 is shown (although the device 103 of FIG. 6 only is represented in FIGS. 7*a* to 7*d*). Each device 102, 103 is configured so that a person can blow their nose on the device 102, 103 to apply nasal discharge to the sampling portion via the hole 21 in the cover layer 2" (FIG. 7*a*). The device 102, 103 can the be folded in half along line 22, generally in a manner as described above with respect to the second embodiment, so that only the backing layer 3" and the capsule 4 are visible (FIG. 7*b*). During folding of the device, the capsule 4 is also folded, and becomes located at an edge of the folded device. The user (e.g., the person undergoing testing) can then press firmly on the capsule 4, which is exposed through the hole 32 in the backing layer 3", causing the capsule 4 to break (FIG. 7*c*). By breaking the capsule 4, buffer solution is released from the capsule 4, which spreads through the sampling portion and mixes with the deposited nasal discharge sample, resulting in a fluidic sample solution. The sample solution may then fluidically transfer from the sampling portion through the label-holding zone to the test zones 14 of the arms 19 to provide a test reading visible through windows 31 in the backing layer 3" (see FIG. 7*d*), generally in a manner set out with respect to the second embodiment. By providing a device 102, 103 with an integral capsule 4, the device 102, 103 may be easier to use. The device 102, 103 may allow testing to be performed without requiring any additional solutions being applied or additional apparatus to be used.

Each device 102, 103 of the third and fourth embodiments carries instructions 23 on its cover layer 2" and backing layer 3". The instructions are located at appropriate positions of the device so that they are visible when they are to be carried out. Furthermore, the device carries advertising 24, which advertising may relate to remedies to cure any ailment for which the user may test positive using the device.

In the various embodiments, the results of the testing may be indicated at the test zones by the revealing of an indicator such as "+" for a positive test and a "−" for a negative test or otherwise. Additionally or alternatively, where a test is positive, a unique code or identifier (not shown) may be revealed.

With reference to FIGS. 8 to 14, a device 200 according to a fifth embodiment of the present invention is now described. The device 200 may be considered to take, generally, a butterfly shape, due to the inclusion in the device of two wings 201, 202, provided by two substantially flat and flexible sampling elements, and a spine 203, provided by an elongate central body, the wings 201, 202 extending from, and being relatively pivotable about, the spine 203. The wings 201, 202 are designed to have a sufficiently large surface area, and to be sufficiently pliable, to flex around a person's nose 204, permitting the person to deposit a nasal mucus sample in a region between the two wings 201, 202, using a nose blowing technique. A simplified drawing of the device 200, with the wings 201, 202 in an open configuration, showing how the device 200 may be brought into a position with a nose 204, is provided in FIG. 8. A more detailed drawing of the device 200, with wings 201, 202 in a closed position, e.g., prior to use of the device, or after receipt of the sample, is shown in FIGS. 9*a* to 9*c*. As can be seen in these Figures, on the outside of each wing 201, 202, a respective finger locator is provided. Each finger locator includes a pad 205 with a hole 206, for receiving a finger or thumb tip 207. By placing the tips 207 of their thumb and forefinger (or other fingers) in the hole 206 of each locator, the user will generally position the device 200 correctly when it is brought into contact with their nose 204 for nose blowing, so that a nasal sample is received at a targeted location of the device 200. Although this device 200 is configured to obtain and test nasal discharge, in alternative embodiments, the device may be configured to obtain and test other biological samples, such as blood, serum, plasma, saliva, sputum, urine, ocular fluid, tears, semen, vaginal discharge, ear secretions, perspiration, mucus, stool, and/or amniotic, spinal, wound, or abscess fluid.

Figure 10:
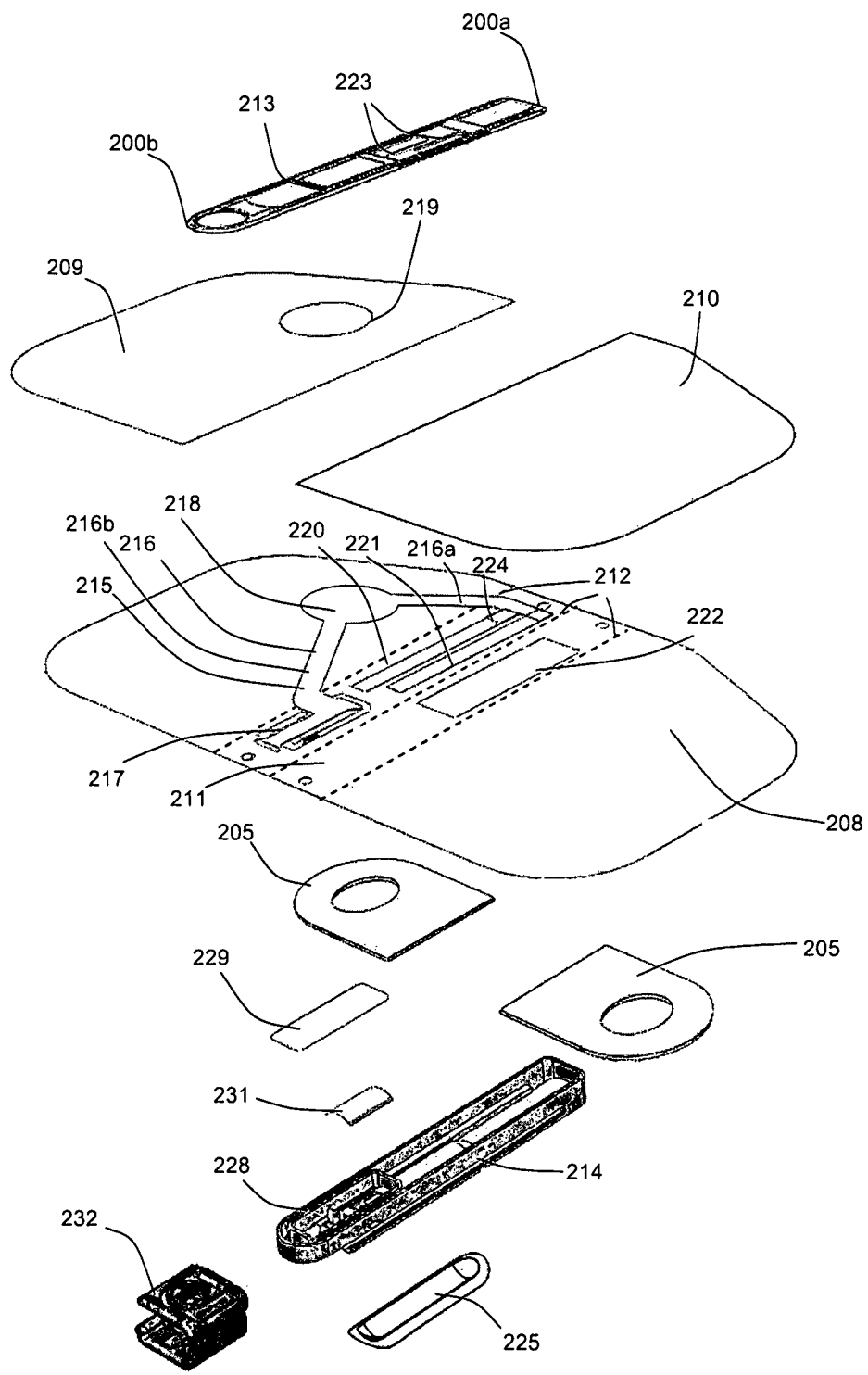
FIG. 10 shows an exploded view of the device of FIG. 8.

FIG. 10 shows an exploded view of the device 200, allowing the various components of the device 200 to be seen in more detail. The two wings 201, 202 are formed from a waterproof backing layer 208 and respective first and second inner layers 209, 210. The backing layer 208 may be formed of plastic, e.g. a polyester sheet. The backing layer 208 is configured to be folded at a central fold region 211 along three fold lines 212, which region 211, when folded, is sandwiched between a top plate 213 and a main body 214 of the spine 203 (see FIG. 9c, for example). The first and second inner layers 209, 210 are mounted on the inner surface of the backing layer 208 at respective sides of the fold region 211. Between the first inner layer 209 and the backing layer 208, an absorbent sample pad 215 is provided. The sample pad 215 provides a lateral flow medium (capillary membrane) and is substantially flexible and absorbent. In this embodiment, the sample pad 215 comprises a substantially v-shaped portion 216 and tongue portion 217 extending from one end of the v-shaped portion 216. At the apex of the v-shaped portion 216, the sample pad 215 comprises a target portion 218, which target portion 218 is substantially oval-shaped in this embodiment.

The first inner layer 209 includes a hole 219 which is slightly smaller than, and located directly over, the target portion 218. The arrangement is such that, with the device 200 correctly located with respect to the nose of a user, through appropriate use of the finger locators, when the user deposits a nasal sample between the wings 201, 202, the nasal sample may pass through the hole 219 and contact the target portion 218. Notably, even if the user were to deposit the sample on the second inner layer 210 of the wing 202 only, by virtue of closing the wings 201, 202 together, the sample may, nevertheless, contact the target portion 218. To ensure that the sample may contact the only the target portion 218 immediately after deposition, and not other elements of the device underneath the inner layers 209, 210, the inner layers 209, 210 may be formed of substantially fluid-resistant material. In combination with the sample pad 215, the first and second inner layers 209, 210 and backing layer 208 may be considered to provide a flexible sampling portion, the sample pad 215 providing an absorbent portion of the sampling portion.

First and second lateral flow test strips 220, 221 are mounted on the backing layer 208 such as to be in fluid engagement with the sample pad 215. Once deposited on the target portion 218 of the sample pad 215, the device is configured such that the sample is transferable by capillary action, from the target portion 218 via a first arm 216a of the v-shaped portion 216, to a first end of each lateral flow test strip 220, 221 adjacent a head end 200a of the device 200. In this embodiment, the lateral flow test strips 220, 221 are conventional test strips, although other test strips or testing means applying the principles of immunochromatography or otherwise may be utilised in this or alternative embodiments. The first and second test strips 220, 221 may be considered to provide a test portion of the device 200.

Referring to FIG. 14, each test strip 220, 221 can include several zones that are arranged sequentially along the length of the strip, including a sample receiving zone 220a, a label-holding zone 220b, a test zone 220c, and a sink 220d. The zones may comprise chemically treated material such as chemically treated nitrocellulose, located on a waterproof substrate. The design is such that the fluid sample, when transferred from the sample pad 215 can continue to travel under capillary action through the sample receiving zone 220a, into the label-holding zone 220b, which contains a substance for labelling of a target analyte, and into the test zone 220c where the sample will contact a test region or stripe 220e containing an immobilized compound capable of specifically binding the labelled target analyte or a complex that the analyte and labelling substance form. The presence of the labelled analyte in the sample generally results in a visually detectable colouring of the stripe 220e.

In addition to the test stripe 220e, a control stripe 220f in the test zone 220 can be provided to indicate that a testing procedure has been performed. The control stripe 220f can be located downstream of the test stripe 220e and is operable to bind and retain the labelling substance. Visible colouring of the control stripe 220f indicates the presence of the labelling substance resulting from the fluid sample flowing through test zone 220c. When the target analyte is not present in the sample, the test stripe 220e shows no visible colouring, but the accumulation of the label in control stripe 220f indicates that the sample has flown through test zone 220c. The sink (absorbent) zone 220d can then capture any excess sample. In this embodiment, the sample pad 215 is directly connected to the sample receiving zone 220a of each strip 220, 221. However, in other embodiments, the sample receiving zone 220a may be omitted and the sample pad 218 may be configured to fluidly connect directly to the label-holding zone.

The test strips 220, 221 are arranged with their elongation directions configured substantially parallel to the fold lines 212, such that the strips can be enclosed by the elongate body of the spine 203 when the backing layer 208 is folded along the fold lines 212. By enclosing the test strips 220, 221 in the spine 203, the strips, which can be relatively rigid and/or brittle in comparison to the sampling portion, may be prevented from breaking. So that the user can see the control and capture lines 220e, 220f of the strips 220, 221 when the fold region 212 is enclosed by the spine 203, a window 222 is provided in the backing layer 208, and two windows 223, one for each test strip, are provided in the top plate 213. In this embodiment, the two test strips 220, 221 are configured to test for the presence of the influenza A and influenza B virus in the sample. However, in the present embodiment or other embodiments, testing for the presence of one of these viruses only, or testing of additional or alternative biological entities, is possible. The device 200 may be modified to include only one test strip, or to include more than two test strips.

The first and second test strips 220, 221 are located in a staggered arrangement. In particular, relative to the second test strip 221, the first test strip 220, which is located nearer to the sample portion 215 than the second test strip 221, is located inwardly from the edge of the backing layer 208 at the head end 200a of the device 200. The particular configuration is intended to ensure that the lengths of the fluid engagement paths between the target portion 218 and the first and second test strips 220, 221 is substantially the same. Accordingly, during testing, sample can be expected to reach corresponding locations of the two strips 220, 221 at substantially the same time such that the results of testing indicated by the two test strips 220, 221 may be presented initially at substantially the same time. To bridge the additional gap between the first arm 216a and the first test strip 220, an inwardly extending projection 224 of the sample pad 215 is provided.

To assist in the transfer of the sample from the target portion 218 to the test strips 2201, 221, a liquid, e.g., a buffer solution, is provided in the device 200. Initially, the liquid is sealed within a first reservoir. With reference to FIG. 11a, for example, the first reservoir is formed between a blister element 225 and a recess 227 in the bottom wall 226 of the main body 214 of the spine 203. The blister element 225 may be formed of Aclar™/polypropylene laminate, for example, and may be attached to bottom wall 226 of the main body via an adhesive. The first reservoir is arranged to hold the liquid underneath a second reservoir of the device 200, the second reservoir being empty of the liquid prior to use of the device 200. With reference to FIGS. 10 and 11b, for example, the second reservoir is formed from a substantially rectangular trough 228 at the top side of the main body 214 and a foil element 229 that seals the top of the trough 228.

In the bottom wall 226 of the main body 214, directly between the first and second reservoirs, an opening 230 is provided. The opening 230 is initially sealed by a pierceable film 231. The pierceable film 231 and opening 230 are designed such that, once the film 231 is pierced, liquid may travel from the first reservoir into the second reservoir. The tongue 217 of the sample pad 215 is configured to extend into the trough 228 of the second reservoir. Accordingly, when the liquid travels into the second reservoir, the liquid can be absorbed, over a period of time, by the tongue 217, whereupon the liquid will travel along the second arm 216b of the sample page 215 to the target portion 218 and combine with the deposited sample. The combined sample and fluid will then travel along the first arm 216a of the sample pad 215 to the test strips 220, 221.

To pierce the film 231, an actuation mechanism is provided. The actuation element is intended to be operated after a sample has been deposited and the wings 201, 202 have been closed together. The actuation mechanism includes a slider 232, slidable along the elongation direction of the spine 203, and a piercing element 233, the piercing element projecting over the hole 230, adjacent the pierceable film 231. The slider 232 has a main body section 234, which is configured to partially surround the spine 203, and a flexible inner flange 235 extending from an inner surface of the main body section 234. The inner flange 235 has a projection 236 at its distal end, the projection 236 being biased by the flange 235 to press against the bottom wall 226 of the spine 203. The spine 203 may be considered to provide a track for controlled movement of the slider 232.

The operation of the actuation mechanism is now described in more detail with reference to FIGS. 12 and 13a to 13c. Referring to FIGS. 12 and 13a, prior to use, the slider 232 is positioned adjacent the tail end 200b of the device 200, with the projection 236 located in a first recess 237 in the bottom wall 226 of the main body 214 such as to prevent the slider 232 from moving freely relative to the spine 203. However, through the user pushing the slider 232 in the elongation direction of the spine 203, in a direction towards the head end 200a of the device, as indicated by arrow A1, the projection can be forced out of the recess 237, allowing the slider to move towards the blister element 225 of the first reservoir. The configuration of engagement surfaces between the projection 236 and recess 237, however, is such as to prevent the slider 232 from being moved in the opposite direction to direction A1.

With reference to FIG. 13b, once the slider 232 reaches the blister element 225, the projection 236 presses against the blister element 225, which element 225 in turn presses against the piercing element 233, forcing a sharp end 238 of the piercing element 233 against the pierceable film 231, causing the film 231 to break. The piercing element 233 is located towards the tail end of the first reservoir, and is therefore actuated almost immediately upon the contact between the projection 236 and the blister element 225. As the slider 232 continues to move in the same direction A1, the projection 236 effectively inverts the blister element 225 towards the bottom of the recess 227, forcing liquid from the first reservoir into the trough 228 of the second reservoir, via the opening 230 (the inversion is not represented in FIG. 13b). Once the film is broken, to ensure that the liquid is not prevented from moving towards the opening 230 by opposing movement of the projection 236 across the blister element 225, which might otherwise invoke a seal between the inverted blister element 225 and the bottom of the recess 227, one or more fluid channels 239 are provided in the bottom surface of the recess 227. The channels 239 ensure that the solution can travel underneath the projection and inverted blister element 225, towards the opening 230.

With reference to FIG. 13c, once the slider 232 passes over the blister element 225, the slider 232 is arranged take up a rest position adjacent the head end 200a of the device 200. To maintain the slider 232 in this position, preventing it from moving freely relatively to the spine 203, the projection 236 is arranged to seat in a second recess 240 and the head end of the slider 200 is arranged to abut a stop element 241 at the head end of the spine 203 such that the slider 232 is prevented from sliding off the spine 203. The configuration of engagement surfaces between the projection 236 and recess 240 is such as to prevent the slider 232 from being returned to the tail end 200b of the device 200. Accordingly, since the slider 232 will be maintained at the head end 200a of the device, it can remain immediately apparent to the user that the device 200 has been used, reducing the likelihood of an attempted re-use of the device 200.

Figure 15:
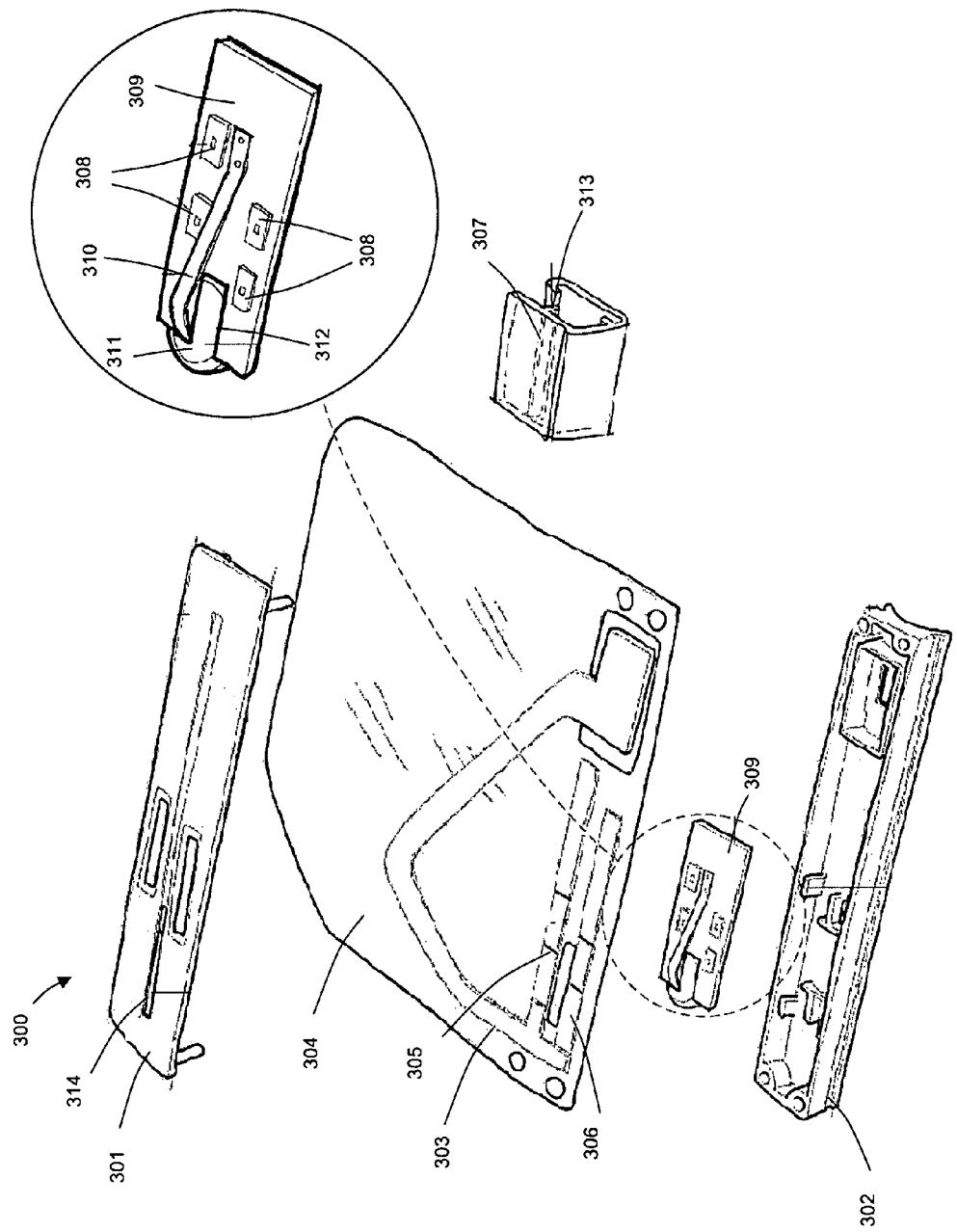
FIG. 15 shows an exploded view of a device according to a sixth embodiment of the present invention.

With reference to FIGS. 15 and 16, a device 300 according to a sixth embodiment of the present invention is now described. Similar to the device 200 of the previous embodiment, the device 300 has a spine formed from a top plate 301 and a main body 302, a sample pad 303 located on a backing layer 304 of a pair of wings (not shown), two lateral flow test strips 305, 306, and a slider 307 for actuating release of a liquid, e.g. buffer solution, to assist in flow of a sample from the sample pad 303 to the test strips 305, 306. On the whole, the configuration and principles of operation of the device 300 are substantially identical to those of the device 200, except for the provision of a mechanism for enhancing the readability of the results of the testing at test zones 305c of the test strips 305, 306. In particular, to enhance readability, in this embodiment a fluorescent material is provided at the label-holding zone 305b of each of the test strips 305, 306 and one or more LEDs 308 (light emitting diodes) are provided to illuminate the fluorescent material when presented at the test zone 305c of each test strip 305, 306. The arrangement is such that the fluorescent material, which may be one or more quantum dots, for example, can be bound to the biological entity under test (target analyte) at the label-holding zone 305b of the test strip 305, and can be retained as part of a labelled complex at the test stripe 305e and/or control stripe 305f of the test zone 305c. The LEDs are configured to emit a wavelength of light suitable for causing fluorescence of the quantum dots, e.g. blue to ultraviolet light. The fluorescent light produced by the quantum dots will be optionally of a visible frequency and thus can provide an enhanced, more clearly visible, line at both the test stripe 305e and control stripe 305f when a particular biological entity is present in the sample. Nonetheless, in alternative embodiments, the fluorescent light may or may not be visible to the naked eye, and an electronic reader may be used to sense the presence or level of fluorescent light.

The electronic reader may be integrated into the device and the results of the testing may be displayed electronically, for example.

In this embodiment, the LEDs 308 are positioned to backlight the test strips 305, 306. In this regard, the LEDs 308 are located on the opposite side of the test strips 305, 306 to the stripes 305e, 305f of the test zone 305c. The positioning of one of the LEDs 308 relative to one of the test strips 305 is represented schematically in FIG. 16. The test strip 305 includes a sample receiving zone 305a, a label-holding zone 305b, a test zone 305c, and a sink 305d, which are mounted on a waterproof substrate 305g. The LED 308 is located to the side of the test strip having the substrate 305g, such that light 305h from the LED is directly incident on the substrate, and particularly underneath the test zone 305c of the substrate. The substrate and test zone are at least partially translucent such that the light 305h from the LED will fall on the stripes 305e, 305f at the test zone and initiate fluorescing of a fluorescent structure located at the stripes 305e, 305f. The fluorescent light 305i may be observed by the user's eye 305j.

This backlighting approach ensures that the LEDs 308 and accompanying electronic componentry will not obscure the user's view of the test zone 305c and allows the LEDs and electronic componentry to be located in the spine 301. In this embodiment, four LEDs 308 are mounted on one side of a circuit board 309 in addition to a conductive lever element, providing an LED switch 310. A battery 311 is located on the opposite side of the circuit board 309, directly below a slot 312 in the circuit board, the slot 312 providing an access opening for the switch 310 to contact the battery 311 in order to complete an electrical circuit to supply energy to illuminate the LEDs 308. The switch 310 is resiliently biased from contact with the battery 311. However, the device 300 is configured such that, after the slider 303 has moved along the spine to actuate release of the liquid in a reservoir, substantially as described with respect to the previous embodiment, it will reach a rest position whereupon a projection 313 on an inner surface of the slider 303 will extend through a slot 314 in the top plate 301 of the spine and press against the switch 310 to complete the electric circuit.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A device for testing a biological sample, the device comprising:
    a rigid housing;
    a sampling portion located outside of the housing, the sampling portion comprising flexible sheet material that projects from and is bendable independently of the housing and is adjustably conformable to a part of a human or animal body, the flexible sheet material having a surface area of at least 20 cm$^2$ and at least a portion of the flexible sheet material being an absorbent target portion configured to receive a biological sample directly from the body;
    a test portion located at least partially inside the rigid housing, the test portion being spaced from the absorbent target portion, the test portion comprising one or more label-holding areas including labels that form labelled complexes with one or more biological entities present in the biological sample and comprising one or more test zones configured to immobilize the labelled complexes to indicate the presence or absence of one or more biological entities in the sample, and
    a fluid flow path, connected between the absorbent target portion and the test portion, that transfers biological sample received at the absorbent target portion to the test portion by capillary action.

2. The device of claim 1, wherein the biological sample comprises any one or more of the following: blood, serum, plasma, saliva, sputum, urine, ocular fluid, tears, semen, vaginal discharge, nasal secretions and droplets, ear secretions, perspiration, mucus, stool, and amniotic, spinal, wound, and abscess fluid.

3. The device of claim 1, wherein the flexible sheet material of the sampling portion is conformable to a nasal region of the body to permit a nasal discharge sample to be provided directly to the absorbent portion.

4. The device of claim 3, wherein the flexible sheet of material of the sampling portion is conformable to contact portions adjacent-an ala or an alar groove on opposite sides of a nose and configured to extend from these contact points on opposite sides of the nose and across a tip of the nose.

5. The device of claim 1, wherein the flexible sheet material of the sampling portion is conformable to an intergluteal cleft to permit a stool sample to be provided directly to the absorbent portion.

6. The device of claim 1 comprising a test layer, wherein the sampling portion and the test portion are comprised in the test layer.

7. The device of claim 6, further comprising a cover layer attached to the test layer, the cover layer defining an opening through which the biological sample is deliverable to a target region of the sampling portion of the test layer.

8. The device of claim 6, further comprising a backing layer attached to the test layer.

9. The device of claim 8, wherein the backing layer is fluid resistant.

10. The device of claim 1 wherein the housing comprises one or more windows through which a reaction at one or more of the test zones to indicate a presence or absence of one or more biological entities in the biological sample is observable.

11. The device of claim 1 wherein the device is foldable to enclose the sampling portion.

12. The device of claim 11 further comprising one or more fixation devices to maintain the device in a folded configuration, the one or more fixation devices comprising: hook and loop fasteners, clips or adhesive.

13. The device of claim 1 further comprising a sealed reservoir, the reservoir containing a liquid releasable from the reservoir to increase fluidity of a biological sample received at the absorbent portion of the sampling portion.

14. The device of claim 13, wherein the device is foldable to enclose the sampling portion, and wherein the reservoir releases the liquid automatically during folding of the device.

15. The device of claim 13, wherein the device is foldable to enclose the sampling portion, and wherein the device comprises a mechanism to release the liquid from the reservoir after folding of the device.

16. The device of claim 13, wherein the reservoir is breakable or burstable to release the liquid.

17. The device of claim 13 wherein the reservoir is at least partially enclosed in the housing.

18. The device of claim 17, wherein the housing comprises an actuation mechanism to break or burst the reservoir to release the liquid.

19. The device of claim 1, wherein the test portion comprises a label-holding zone including a labelling substance configured to bind a fluorescent structure to a biological entity in the biological sample; and the device further comprises one or more light sources operable to emit light at a wavelength suitable for causing the fluorescent structure to fluoresce.

20. The device of claim 19, wherein the one or more light sources are configured to backlight the one or more test zones.

21. The device of claim 1, wherein the test portion comprises at least one lateral flow test strip.

22. The device of claim 1, wherein the sampling portion comprises two flexible wings, each wing extending from, and being pivotable relative to, the housing.

23. A test device for receiving and testing a nasal discharge sample from a nose, the test device comprising:
  a housing;
  a sampling portion projecting from the housing, the sampling portion comprising flexible sheet material defining two flexible wings, the two flexible wings being pivotable relative to the housing and configured to be positioned on opposite sides of the nose, the flexible sheet material having a surface area of at least 20 cm$^2$ and comprising an absorbent target portion to receive a nasal discharge sample from the nose; and
  a test portion located at least partially inside the housing, the test portion being spaced from the absorbent target portion, the test portion comprising one or more label-holding areas including labels that form labelled complexes with one or more biological entities present in the biological sample and comprising one or more test zones configured to immobilize the labelled complexes to indicate the presence or absence of one or more biological entities in the sample,
  a sealed reservoir containing liquid, the sealed reservoir located at least partially inside the housing;
  a mechanism operable to break or burst the reservoir to release the liquid from the reservoir, wherein the released liquid is transferred to the absorbent portion by capillary action to increase the fluidity of nasal discharge sample received at the absorbent portion; and
  a fluid flow path, connected between the absorbent target portion and the test portion, that transfers nasal discharge sample received at the absorbent portion to the test portion by capillary action.

* * * * *